(12) United States Patent
Bryan et al.

(10) Patent No.: US 12,041,997 B2
(45) Date of Patent: Jul. 23, 2024

(54) REDUCING BRAIN INJURY BY LIMITING BRAIN MOTION DURING SUDDEN DECELERATION OR ACCELERATION OF THE HEAD

(71) Applicant: PreActive Technologies Inc., Kirkland, WA (US)

(72) Inventors: Vincent E. Bryan, Quincy, WA (US); Randal P. Ching, Seattle, WA (US); Daniel Reed Baker, Seattle, WA (US)

(73) Assignee: Preactive Technologies Inc., Kirkland, WA (US)

( * ) Notice: Subject to any disclaimer, the term of this patent is extended or adjusted under 35 U.S.C. 154(b) by 757 days.

(21) Appl. No.: 16/171,184

(22) Filed: Oct. 25, 2018

(65) Prior Publication Data

US 2019/0059495 A1  Feb. 28, 2019

Related U.S. Application Data

(63) Continuation-in-part of application No. 15/467,912, filed on Mar. 23, 2017.
(Continued)

(51) Int. Cl.
*A42B 3/04* (2006.01)
*A42B 3/30* (2006.01)
(Continued)

(52) U.S. Cl.
CPC ............ *A42B 3/046* (2013.01); *A42B 3/30* (2013.01); *A61B 5/11* (2013.01); *A61B 17/1325* (2013.01);
(Continued)

(58) Field of Classification Search
None
See application file for complete search history.

(56) References Cited

U.S. PATENT DOCUMENTS

| | | |
|---|---|---|
| 3,735,398 A * | 5/1973 | Ross .............. B60K 31/0008 342/21 |
| 4,907,602 A | 3/1990 | Sanders |

(Continued)

FOREIGN PATENT DOCUMENTS

| | | |
|---|---|---|
| EP | 3171768 A1 | 5/2017 |
| EP | 3302691 B1 | 7/2019 |

(Continued)

OTHER PUBLICATIONS

Prabhakar, Hemanshu et al. "Intracranial pressure changes during Valsalva Manoevre in Patients Undergoing a Neuroendoscopic Procedure" 2007 (Year: 2007).*

(Continued)

*Primary Examiner* — Bradley H Philips
*Assistant Examiner* — Savannah L Gabriel
(74) *Attorney, Agent, or Firm* — Fenwick & West LLP

(57) ABSTRACT

A brain injury reduction system provides a protective measure to reduce severity of brain injury caused by collision or blast. A sensing device of the system detects an impending or occurring event (e.g., collision or blast) in an environment surrounding the individual and sends information about the event to a controller of the system. The sensing device can be stationary or moves with the individual. Based on the information, the controller determines whether the event will likely cause brain injury to the individual. If so, the controller sends an instruction to an actuation device of the system to activate the protective measure. The actuation device uses transcutaneous electrodes to electrically simulate glottis closure and contraction of the abdominal musculature to induce a Valsalva-like maneuver. The Valsalva-like maneuver can increases the stiffness of the brain tissues in the intracranial compartment, and thus reduces the susceptibility of the brain tissues to deformation.

26 Claims, 15 Drawing Sheets

Related U.S. Application Data

(60) Provisional application No. 62/462,906, filed on Feb. 23, 2017, provisional application No. 62/496,899, filed on Nov. 1, 2016, provisional application No. 62/391,302, filed on Apr. 25, 2016.

(51) Int. Cl.

| | | |
|---|---|---|
| *A61B 5/11* | (2006.01) | |
| *A61B 17/132* | (2006.01) | |
| *A61B 17/135* | (2006.01) | |
| *A61N 1/36* | (2006.01) | |
| *A61B 5/00* | (2006.01) | |
| *A61N 1/04* | (2006.01) | |

(52) U.S. Cl.
CPC ........ *A61B 17/135* (2013.01); *A61B 17/1355* (2013.01); *A61N 1/36003* (2013.01); *A61B 5/4836* (2013.01); *A61B 5/6803* (2013.01); *A61B 5/7267* (2013.01); *A61N 1/0452* (2013.01); *A61N 1/0456* (2013.01); *A61N 1/0484* (2013.01); *A61N 1/36014* (2013.01)

(56) References Cited

U.S. PATENT DOCUMENTS

| | | | |
|---|---|---|---|
| 5,016,647 A | 5/1991 | Sanders | |
| 5,038,796 A | 8/1991 | Axelgaard et al. | |
| 5,048,522 A | 9/1991 | Petrofsky | |
| 5,397,337 A | 3/1995 | Jaeger et al. | |
| 5,467,766 A | 11/1995 | Ansite et al. | |
| 5,490,820 A * | 2/1996 | Schock | A61H 31/008 |
| | | | 601/1 |
| 5,546,609 A | 8/1996 | Rush | |
| RE36,120 E | 3/1999 | Karell | |
| 5,897,579 A | 4/1999 | Sanders | |
| 6,213,960 B1 | 4/2001 | Sherman et al. | |
| 6,463,327 B1 * | 10/2002 | Lurie | A61M 16/209 |
| | | | 607/42 |
| 6,594,614 B2 | 7/2003 | Studt et al. | |
| 7,890,178 B2 | 2/2011 | Testerman et al. | |
| 7,954,900 B2 | 6/2011 | Shantha et al. | |
| 8,172,769 B2 | 5/2012 | Lenhardt et al. | |
| 8,588,919 B2 | 11/2013 | Li | |
| 8,702,516 B2 | 4/2014 | Bentley et al. | |
| 9,226,707 B2 | 1/2016 | Huang | |
| 9,272,139 B2 | 3/2016 | Hamilton et al. | |
| 9,474,898 B2 | 10/2016 | Gozani et al. | |
| 9,616,234 B2 | 4/2017 | Harry et al. | |
| 9,884,178 B2 | 2/2018 | Bouton et al. | |
| 9,884,179 B2 | 2/2018 | Bouton et al. | |
| 10,001,346 B2 | 6/2018 | Augustine et al. | |
| 10,195,010 B2 | 2/2019 | Sanders | |
| 10,285,934 B1 | 5/2019 | Sharma et al. | |
| 10,335,396 B2 | 7/2019 | Nemechek | |
| 2003/0182040 A1 * | 9/2003 | Davidson | A41D 13/018 |
| | | | 701/45 |
| 2004/0181161 A1 | 9/2004 | Addington et al. | |
| 2005/0283205 A1 * | 12/2005 | Lee | A61B 5/389 |
| | | | 607/48 |
| 2007/0293926 A1 * | 12/2007 | Dunlay | A61N 1/0548 |
| | | | 607/148 |
| 2008/0215128 A1 | 9/2008 | Rainey et al. | |
| 2010/0063736 A1 | 3/2010 | Hoetzer | |
| 2010/0303289 A1 | 12/2010 | Polzin et al. | |
| 2010/0312139 A1 | 12/2010 | Dash et al. | |
| 2011/0082514 A1 | 4/2011 | Libbus et al. | |
| 2011/0089725 A1 | 4/2011 | Shantha et al. | |
| 2011/0226264 A1 | 9/2011 | Friedman et al. | |
| 2011/0276107 A1 * | 11/2011 | Simon | A61N 2/02 |
| | | | 607/46 |
| 2012/0116291 A1 * | 5/2012 | Mogi | A61G 7/05792 |
| | | | 604/23 |
| 2013/0197321 A1 | 8/2013 | Wilson | |
| 2013/0239835 A1 * | 9/2013 | Tillotson | F41H 11/02 |
| | | | 102/215 |
| 2013/0274615 A1 | 10/2013 | Ben-Ari et al. | |
| 2013/0296751 A1 | 11/2013 | Martin et al. | |
| 2013/0310909 A1 | 11/2013 | Simon et al. | |
| 2014/0142616 A1 | 5/2014 | Smith | |
| 2014/0236058 A1 | 8/2014 | Lee | |
| 2014/0276278 A1 | 9/2014 | Smith et al. | |
| 2014/0323921 A1 * | 10/2014 | Huang | A42B 3/0473 |
| | | | 600/587 |
| 2014/0343599 A1 * | 11/2014 | Smith | F41H 1/00 |
| | | | 606/202 |
| 2014/0371545 A1 | 12/2014 | Ben-Ari et al. | |
| 2015/0120007 A1 | 4/2015 | Guez et al. | |
| 2015/0321000 A1 * | 11/2015 | Rosenbluth | A61N 1/18 |
| | | | 607/48 |
| 2015/0335288 A1 | 11/2015 | Toth et al. | |
| 2016/0000367 A1 | 1/2016 | Lyon | |
| 2016/0309808 A1 * | 10/2016 | Armour | A61F 5/055 |
| 2016/0310730 A1 * | 10/2016 | Martins | A61M 16/024 |
| 2017/0006931 A1 | 1/2017 | Guez et al. | |
| 2017/0231490 A1 | 8/2017 | Toth et al. | |
| 2017/0304140 A1 | 10/2017 | Bryan et al. | |
| 2018/0001086 A1 | 1/2018 | Bartholomew et al. | |
| 2018/0008155 A1 | 1/2018 | Melker et al. | |
| 2018/0154140 A1 | 6/2018 | Bouton et al. | |
| 2018/0178008 A1 | 6/2018 | Bouton et al. | |
| 2018/0178013 A1 | 6/2018 | Bouton et al. | |
| 2018/0214117 A1 | 8/2018 | Oura | |
| 2018/0353086 A1 | 12/2018 | Turner et al. | |
| 2019/0001126 A1 | 1/2019 | Evans et al. | |
| 2019/0001127 A1 | 1/2019 | Evans et al. | |
| 2019/0059495 A1 | 2/2019 | Bryan et al. | |
| 2019/0126018 A1 | 5/2019 | Browd et al. | |
| 2019/0262212 A1 * | 8/2019 | Schroeder | A61H 1/0296 |

FOREIGN PATENT DOCUMENTS

| | | | |
|---|---|---|---|
| WO | WO 2011/044173 A1 | 4/2011 | |
| WO | WO 2015/061663 A1 | 4/2015 | |
| WO | WO 2017/087556 A1 | 5/2017 | |
| WO | WO 2018/085439 A1 | 5/2018 | |
| WO | WO 2018/213456 A1 | 11/2018 | |

OTHER PUBLICATIONS

Dunn, L. T., "Raised Intracranial Pressure," Journal of Neurology, Neurosurgery & Psychiatry, vol. 73, Sep. 1, 2002, pp. 23-27.

Tsujimura, T. et al., "Laryngeal and tracheal afferent nerve stimulation evokes swallowing in anaesthetized guinea pigs," The Journal of Physiology, Jul. 15, 2013, pp. 4667-4679.

United States Office Action, U.S. Appl. No. 15/467,912, filed Jul. 21, 2020, 33 pages.

European Patent Office, Extended European Search Report and Opinion, EP Patent Application No. 17790057.8, Dec. 6, 2019, eight pages.

European Patent Office, Extended European Search Report and Opinion, EP Patent Application No. 19205341.1, Feb. 26, 2020, seven pages.

PCT International Search Report and Written Opinion, PCT/US2017/023889, Jun. 16, 2017, 16 pages.

Porth, C. J. et al., "The Valsalva Maneuver: Mechanisms and Clinical Implications," Heart Lung, Sep. 13, 1984, Abstract Only.

Schaller, B., "Physiology of Cerebral Venous Blood Flow: From Experimental Data in Animals to Normal Function in Humans," Brain Research Reviews, Apr. 26, 2004, vol. 46, pp. 243-260.

United States Office Action, U.S. Appl. No. 15/467,912, filed Jan. 27, 2020, 28 pages.

United States Office Action, U.S. Appl. No. 15/467,912, filed Jun. 9, 2021, 14 pages.

* cited by examiner

REDUCING BRAIN INJURY BY LIMITING BRAIN MOTION DURING SUDDEN DECELERATION OR ACCELERATION OF THE HEAD

CROSS-REFERENCE TO RELATED APPLICATIONS

This application is a continuation-in-part application of Ser. No. 15/467,912, filed on Mar. 23, 2017, which claims the benefit of U.S. Provisional Application No. 62/391,302 filed on Apr. 25, 2016, U.S. Provisional Application No. 62/496,899 filed on Nov. 1, 2016, and U.S. Provisional Application No. 62/462,906 filed on Feb. 23, 2017. The content of each of the above referenced applications is incorporated by reference in its entirety.

TECHNICAL FIELD

The disclosure generally relates to medical devices, and more specifically to a system for reducing brain injury in an individual.

BACKGROUND

Sudden decelerating or accelerating head movements, which may be as a result of direct head impact in sports games (e.g., football), vehicular crashes, accidents (e.g., slips and falls), or on the battlefield (such as blast), may produce immediate and/or progressive long term devastating brain injury. Such brain injury may be related to excessive brain movement inside of the calvarium which is associated with certain detrimental effects. The excessive brain movement can be at both macroscopic and microscopic levels. Histological studies suggest that such injury may take place at the cellular level and adversely affects neuronal axons. As a result, locally damaging chemical and inflammatory responses may be set in motion. These pathophysiological events appear to be related to kinematic movement (such as sudden acceleration or deceleration) of the head (including brain tissues and fluids) as well as the resulting momentum changes to the brain inside of the calvarium, which may induce deleterious stretching or strain in the brain tissues.

Conventional efforts have been made to reduce head injury from forceful blows, specifically skull fractures, by means of helmets which have been designed to attenuate the transfer of external energy to the head from a collision. One example includes the design of rigid exterior helmets. Despite this effort, brain injuries continue to occur. More recent helmet designs using flexible exterior, shock absorbing, multilayer helmet designs with novel flexible resilient interior baffles may offer better protection to the skull. However, these conventional approaches do not offer a means to limit distortion or deformation of brain tissues, and as such, brain injury as a result of forceful blows to the head remains a concern.

SUMMARY

Embodiments of the invention include a brain injury reduction system that provides a protective measure to an individual that is currently experiencing or will undergo acceleration or deceleration of the head (e.g., resulting from impact or a blast pressure wave from an explosive device). A protective measure provided by the brain injury reduction system reduces an individual's brain injury at macroscopic and/or microscopic levels relative to the calvarium during events that cause sudden decelerating/accelerating head movements or exert impact or blast force on the individual's head. Specifically, the brain injury reduction system reduces brain injury by impeding venous drainage. The reduced cerebral venous drainage reduces the movement of the brain within the calvarium. This reduction in brain motion within the calvarium, in turn, results in less distortion or deformation of the brain tissues (straining or stretching of the tissues).

Generally, venous drainage from the intracranial compartment occurs via the jugular veins, and more specifically the internal jugular veins (IJV), when an individual is supine, and via the paravertebral venous plexus (PVP), also referred to as the vertebral venous plexus (VVP), when upright. When an impact to the head (or blast pressure wave) occurs, venous drainage from the intracranial compartment occurs and the properties of the brain tissue in the intracranial space within the head allow the brain to displace (or distort or deform) within the calvarium. If the impact or blast force is high, then the corresponding distortion or deformation of the brain tissues may also be high, surpassing threshold levels for injury to occur. However, a reduction in venous drainage from the intracranial compartment (just prior to and/or during an impact or blast) could reduce brain movement (at both the macroscopic and microscopic levels) that is a consequence of the sudden acceleration or deceleration movement of the individual's head. The reduction in venous drainage just prior to and/or during an impact or blast can induce cerebral venous congestion, effectively increasing the stiffness or rigidity of the brain tissues in the intracranial compartment, and thus reduce the susceptibility of the brain tissues to deformation. For an individual in an upright position, reduction of venous drainage through the VVP can be achieved by inducing a gag reflex or a Valsalva maneuver (or through other mechanisms that may reduce this cerebral venous drainage). For an individual in a supine position, reduction of venous drainage through one or both of the IJV and external jugular veins (EJV) can be achieved through external compression of the IJV and EJV, respectively.

The brain injury reduction system decreases drainage of venous blood out of the intracranial compartment through the VVP and the IJVs at or just before the occurrence of a sudden acceleration or deceleration of an individual's head (e.g., kinematic movements resulting from an impact or blast). Specifically, the brain injury reduction system includes components that may be worn by or proximal to the individual such as a wearable head-impact and/or position-tracking sensing device (e.g., miniature sensors mounted into a helmet, mouthguard, headband, vehicle, or drone) as well as one or more wearable actuation devices that are configured to reduce cerebral venous drainage through the IJVs or VVP. For example, a wearable actuation device can be configured to reside around the neck of the individual and expand to externally compress the IJVs when required. As another example, a wearable actuation device can be configured to stimulate a gag reflex or a Valsalva-like maneuver.

The Valsalva maneuver is a physiological protective measure that is readily available and often instinctively activated when an individual is able to anticipate an impending event (e.g., collision or blast) that may cause injurious forces to the individual. The Valsalva maneuver induces cerebral venous congestion, effectively increasing the stiffness of the brain tissues in the intracranial compartment, and thus reduces the susceptibility of the brain tissues to deformation. In cases where an individual is unable able to anticipate an impending impact or blast, the brain injury reduction system can induce the anticipatory response to activate this physiological protective measure. For example, the brain injury reduction system uses electrical stimulation to cause glottis closure and cause contraction of the abdominal musculature which, together, may result in a Valsalva-like maneuver.

Each of the devices are communicatively coupled with one another such that each of the one or more wearable actuation devices can instantaneously provide or activate the protective measure in response to a detected event, such as an impending collision or blast, by the wearable or proximal sensing device or other triggering devices, such as an adjacent system triggering protective measures of a plurality of people in one area (e.g., occupants in a blast zone). The brain injury reduction system can subsequently terminate the protective measure after the occurrence of the collision or blast, or after a pre-determined endpoint occurs.

BRIEF DESCRIPTION OF THE DRAWINGS

The disclosed embodiments have advantages and features which will be more readily apparent from the detailed description, the appended claims, and the accompanying figures (or drawings). A brief introduction of the figures is below.

FIG. (FIG.) 1A illustrates an overall system environment for providing a protective measure for reducing brain injury in an individual, in accordance with an embodiment.

Figure 1A:
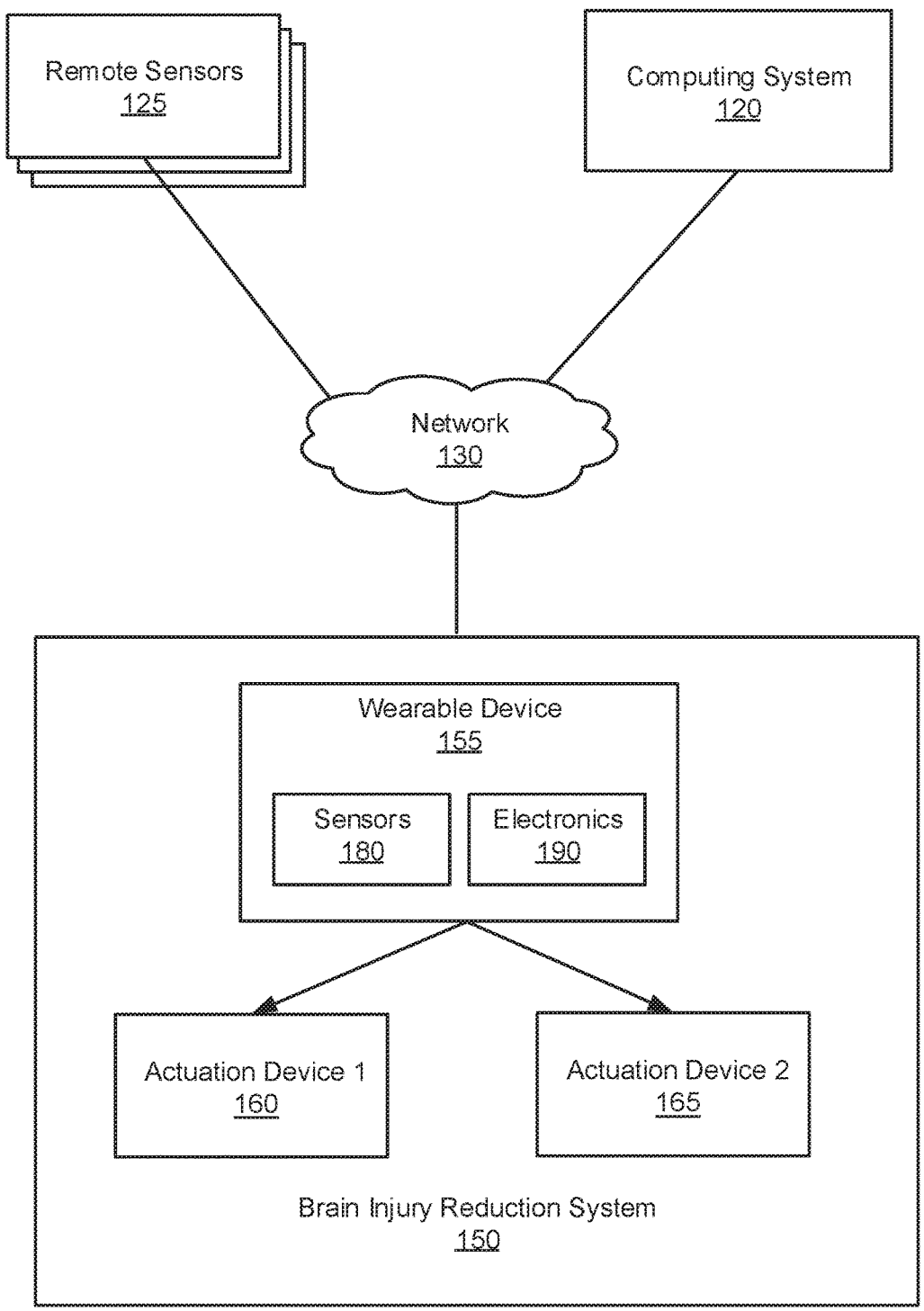
FIGS. 1B and 1C each illustrate components of the brain injury reduction system worn by an individual, in accordance with an embodiment.

The Figures (FIGs.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

DETAILED DESCRIPTION

The FIGs. depict embodiments of the disclosed system (or method) for purposes of illustration only. One skilled in the art will readily recognize from the following description that alternative embodiments of the structures and methods illustrated herein may be employed without departing from the principles described herein.

Reference will now be made in detail to several embodiments, examples of which are illustrated in the accompanying figures. It is noted that wherever practicable similar or like reference numbers may be used in the figures and may indicate similar or like functionality. For example, a letter after a reference numeral, such as "320a," indicates that the text refers specifically to the element having that particular reference numeral. A reference numeral in the text without a following letter, such as "320," refers to any or all of the elements in the figures bearing that reference numeral (e.g. "actuating component 320" in the text refers to reference numerals "actuating component 320a" and/or "actuating component 320b" in the figures).

Overall System Environment

FIG. 1A illustrates an overall system environment 100 for providing a protective measure for reducing brain injury in an individual, in accordance with an embodiment. Generally, the overall system environment 10 includes a brain injury reduction system 150, a computing system 120, and remote sensors 125 that are interconnected through a network 130. As shown in FIG. 1A, the brain injury reduction system 150 may further include a wearable device 155, an actuation device 1 (160), and an actuation device 2 (165).

Although the illustrated environment 100 may include the elements shown in FIG. 1, in other embodiments the environment 100 may include different elements (e.g., additional or fewer elements). In one embodiment, the system environment 100 may include multiple brain injury reduction systems 150 in communication with one another, the computing system 120, and remote sensors 125 through the network 130. In some embodiments, the system environment 100 does not include a computing system 120 and/or the remote sensors 125. In various embodiments, the brain injury reduction system 150 includes one of the two actuation devices 160 or 165, or includes more than two actuation devices (e.g., three, four, or more actuation devices). In various embodiments, there are no sensors and/or electronics in the wearable device, and instead there are only one or more actuation devices that are actuated by some other mechanism (e.g., the remote sensors or computing system), or the actuation devices remain in an always on position such that an actuation signal is not needed. Furthermore, the functionalities of each element may be distributed differently among the elements in other embodiments.

Example Brain Injury Reduction System

As shown in FIG. 1A, a brain injury reduction system 150 includes a wearable device 155 as well as one or more actuation devices 160, 165. In various embodiments each of the wearable device 155 and actuation devices 160,165 are wearable and configured to be worn by a particular individual. As such, a brain injury reduction system 150 is responsible for reducing brain injury in a particular individual. In various embodiments, each of the wearable device 155, actuation device 1 (160), and actuation device 2 (160) includes wearable housings that contain components of each of the wearable device 155, actuation device 1 (160), and actuation device 2 (160).

Notably, the subsequent disclosure that describes each of the wearable device 155, actuation device 1 (160) and actuation device 2 (165) will refer to each device in one of a rest state or an actuated state. The rest state refers to the default state of each device when a protective measure is not provided. Each device can transition to an actuated state when a protective measure is needed. Specifically, when each device is in an actuated state, the brain injury reduction system 150 maintains (or increases) the venous pressure in the brain in the individual, thereby reducing brain injury due to decelerating or accelerating head motion (e.g., resulting from head impact or a pressure wave from an explosive device).

In one embodiment, the wearable device 155 is headwear, such as a helmet, worn by an individual. In other embodiments, the wearable device 155 can be worn on another anatomical location (e.g., chest, neck, hip, extremities such as arms or legs, and the like) of the individual. The wearable device 155 can be a wearable sensing device that includes sensors 180 and electronics 190. The sensors 180 of the wearable device 155 can be configured to detect an occurring or impending collision. The electronics 190 of the wearable device 155 may include one or more of a power source, processor, or communication hardware. Therefore, the electronics 190 of the wearable device 155 enable the wearable device 155 to communicate with the computing system 120 and/or remote sensors 125 through the network 130. Additionally, the electronics 190 of the wearable device 155 can enable the wearable device 155 to communicate with the actuation devices 160 and 165 (e.g., through Bluetooth, near field communication (NFC), WiFi, 2G, 3G, 4G, long-term evolution (LTE), a proprietary communication system, and/or an encrypted communications system). Further description regarding the sensors 180 and electronics 190 of the wearable device 155 are described below in reference to FIG. 2C.

Actuation device 1 (160) and an actuation device 2 (165) are each configured to stimulate and cause a type of an anatomical or physiological response in an individual that assists in the reduction of brain injury. In some embodiments, the brain injury reduction system 150 includes a single actuation device 160. In other embodiments, the brain injury reduction system 150 includes multiple actuation device 1 (160) that each causes or reinforces a first type of anatomical or physiological response in the individual and/or multiple actuation device 2 (165) that each causes a second type of anatomical or physiological response in the individual.

Figure 1B:
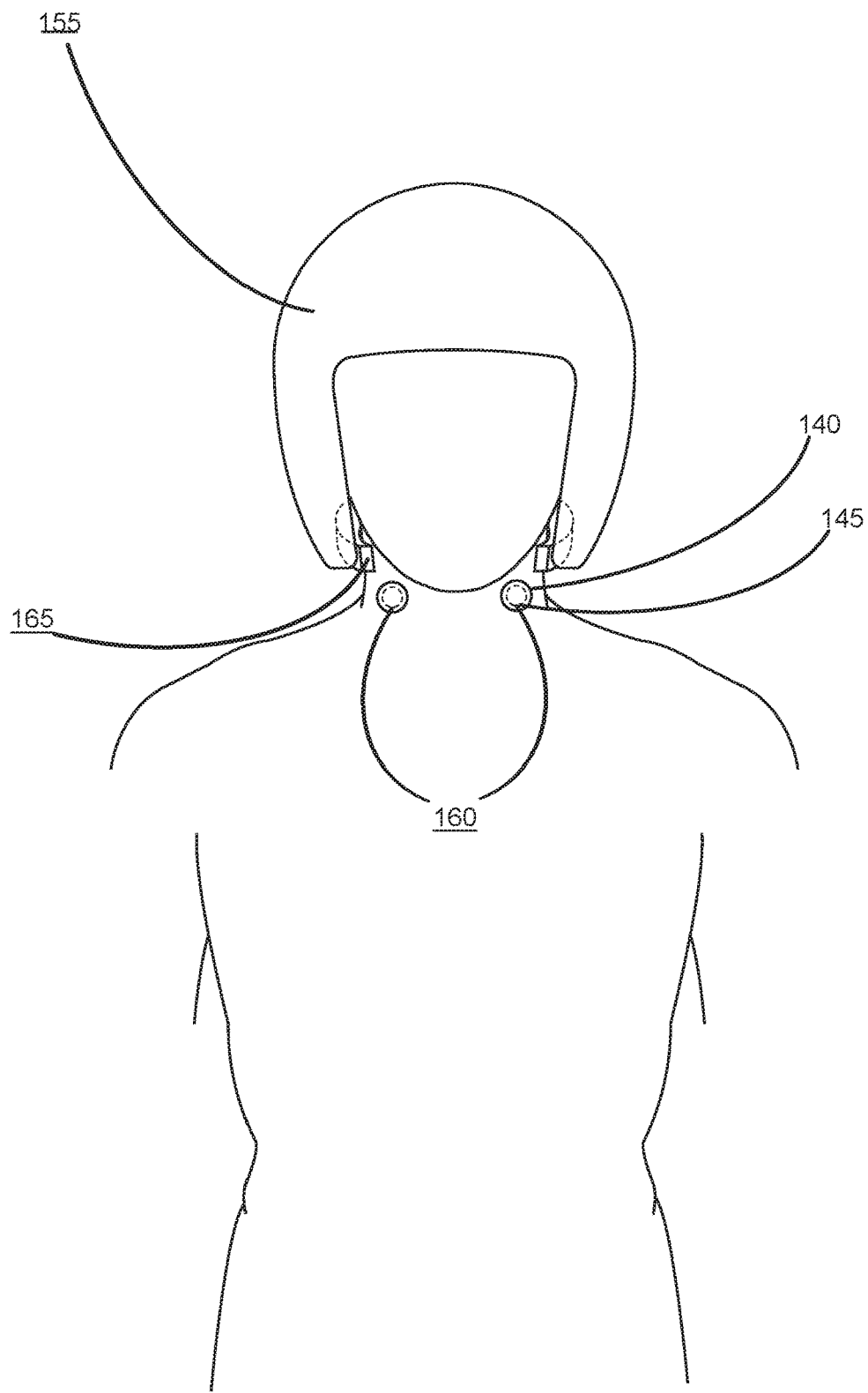
Figure 1C:
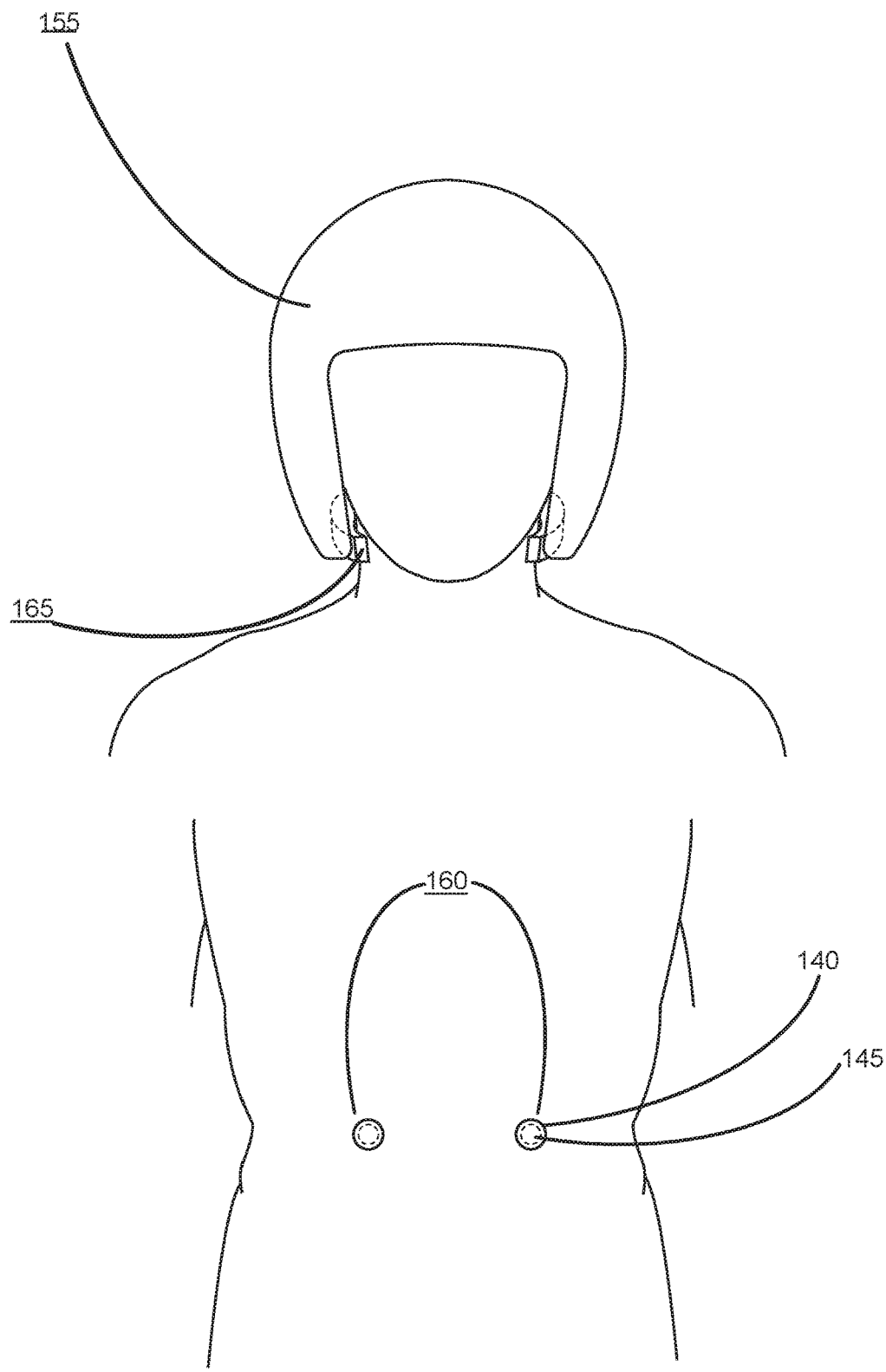

Reference is now made to FIG. 1B and FIG. 1C, which each illustrates components of the brain injury reduction system 150 worn by an individual, in accordance with an embodiment. Specifically, FIG. 1B depicts a wearable device 155 as a helmet, actuation device 1 (160), and actuation device 2 (165) that is configured to circumferentially surround a portion of the neck of the individual. In some embodiments, a wearable device 155 can be a wearable garment such as a shirt (e.g., football jersey), pants, shoes, protective wear (e.g., brace, pads), and the like.

Referring first to actuation device 2 (165) shown in FIG. 1B, the actuation device 2 (165) may be situated around the neck of the individual so as to be in close proximity to the skin of the individual under which the IJVs reside. In some embodiments, the actuation device 2 (165) is physically coupled to the wearable device 155 through one of straps, buckles, adhesives, buttons, and the like. In various embodiments the actuation device 2 (165) is removably coupled to wearable device 155. In other embodiments, the actuation device 2 (165) is a standalone device and separate from the wearable device 155.

When in an actuated state, actuation device 2 (165), may change its configuration to physically compress the IJVs, thereby reducing venous drainage through the IJV. For example, actuation device 2 (165) may include protrusions that extend from the housing of the actuation device 2 (165) to externally compress the IJVs. An example actuation device 2 (165) is described in further detail below in regards to FIG. 3.

Referring now to actuation device 1 (160), it is configured to cause one of a gag reflex or a Valsalva-like maneuver in the individual when in an actuated state. Therefore, actuating the actuation device 1 (160) causes a reduction in venous drainage through the PVP. As depicted in FIG. 1B, actuation device 1 (160) can include a pair of stimulation structures such as electrode leads 145 in contact with the skin of the individual. These may be neuromuscular stimulation structures that are configured to stimulate a nerve and/or a muscle. Additionally, the electrode leads 145 may be located on or within an electrode housing 140. As an example, an electrode housing 140 may be an electrode pad that houses the electrode leads 145 such that the electrode housing 140 is in contact with the individual's skin.

In some embodiments, the electrode leads 145 or the electrode housing 140 is attached to the skin through any one of adhesives or gels. Such adhesives or gels can hold the electrode leads 145 or the electrode housing 140 in contact with the skin of the individual and, in some embodiments, can further improve the conductivity of the skin. In various embodiments, instead of a pair of electrode leads 145, a single electrode lead 145 in contact with the skin of the individual is sufficient to provide a stimulation. The electrode leads 145 may be connected (e.g., wired) to a power source such as a minimal battery such that the actuation device 1 (160) remains non-intrusive.

As depicted in FIG. 1B, the electrode leads 145 and the electrode housing 140 of the actuation device 1 (160) are spherical in shape. However, in other embodiments, the electrode leads 145 and electrode housing 140 may be square, rectangular, triangular, oval, hexangular, or another polygon in shape. In various embodiments, the electrode leads 145 are between 1 millimeter and 10 millimeters in diameter. In other embodiments, the electrode leads 145 may be larger, for example, between 10 millimeters and 10 centimeters in diameter.

Each electrode lead 145 may be configured to provide a transcutaneous stimulation to a corresponding nerve located beneath the skin. Therefore, actuation of the electrode leads 145 (e.g., providing an electric input) can stimulate a nerve and result in a desired anatomic response. Specifically, actuation device 1 (160) depicted in FIG. 1B may contact the skin of the individual located external or near to the laryngeal nerves and therefore causes a glottis closure as a result of stimulating the laryngeal nerves.

In some embodiments, electrodes can be in-dwelling or implanted electrodes. There can also be other transcutaneous or implantable nerve- or muscle-stimulating components. These components may be connected to power supplies via wire connections and/or driven by electromagnetic waves such as radio frequency waves to an antenna system implanted with the electrode.

Referring now to FIG. 1C, the actuation device 1 (160) may be placed in contact with the skin of the individual at a different anatomical location. Specifically, as shown in FIG. 1C, actuation device 1 (160) may include stimulation structures such as electrode leads 145 that are in contact with the skin of the individual located above or near the thoraco-abdominal nerves. Also depicted in FIG. 1C are electrode housings 145 that are configured to house the electrode leads 140. In this scenario, actuation of the actuation device 1 (160) causes a Valsalva-like maneuver as a result of stimulating the thoraco-abdominal nerves or the rectus abdominal muscles directly.

Although FIG. 1B and FIG. 1C each depict two different embodiments of actuation device 1 (160), in various embodiments, the actuation device 1 (160) may include a first set of electrode leads 145 in contact with the skin of the individual that is configured to stimulate the laryngeal nerves as well as a second set of electrode leads 145 in contact with the skin of the individual that is configured to stimulate the thoraco-abdominal nerves. As such, actuation of actuation device 1 (160) can cause both a gag reflex and a Valsalva-like maneuver.

The actuation device 1 (160) and the actuation device 2 (165) may each contain electronics that enable each actuation device 160 and 165 to communicate with the wearable helmet 155. More specifically, the actuation device 1 (160) and the actuation device 2 (165) can receive input from the wearable helmet 155 through the electronics that cause each actuation device 160 and 165 to actuate. Altogether, actuation of one or both of actuation device 1 (160) and actuation device 2 (165) maintains or increases the venous pressure within the individual's brain due to a reduction in venous drainage. Additional embodiments of actuation devices 160 and 165 are described in further detail below.

Example Remote Sensors

Figure 2A:
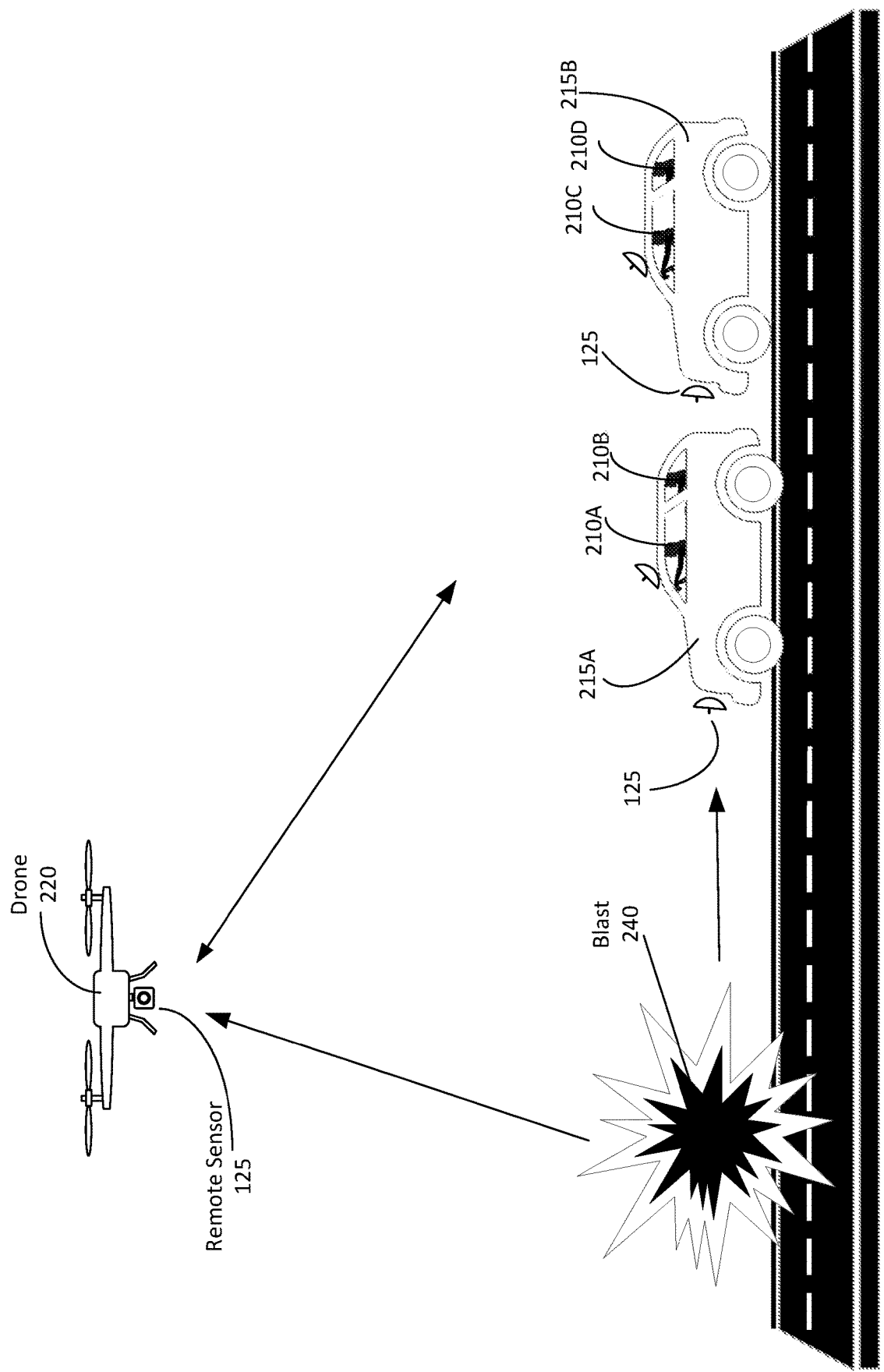
FIGS. 2A and 2B each illustrate an example remote sensor, in accordance with an embodiment.
Figure 2B:
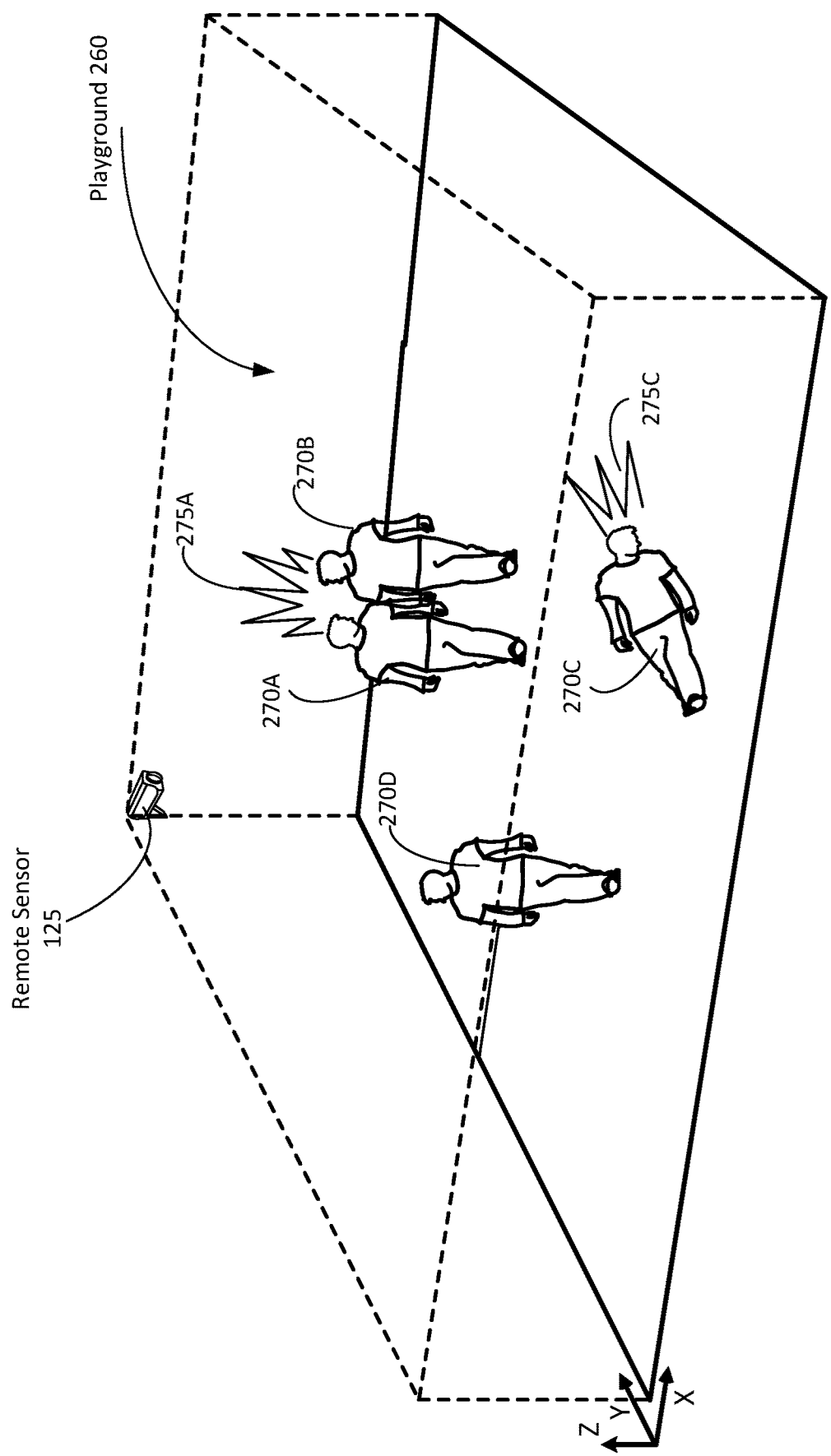

FIGS. 2A and 2B each illustrate an example remote sensor, in accordance with an embodiment. A remote sensor 125 detects events in an environment surrounding an individual to be protected from brain injury (e.g., an individual using the wearable device 155) that may cause brain injury of the individual. For example, a remote sensor 125 may be a sensor capable of capturing signals including, but not limited to, photons, electromagnetic radiation, and acoustic signals. For example, a remote sensor 125 may be an image sensor that collects light (or other types of radiation, e.g., thermal radiation) in the environment and generates images data based on the collected light. In one embodiment, a remote sensor 125 is an ultraviolet (UV)-infrared (IR) sensor that is sensitive to both UV and IR wavelengths. Such a UV-IR sensor can be used to detect a blast or explosion.

FIG. 2A shows remote sensors 125 that move with individuals 210A-D to be protected from brain injury, in accordance with an embodiment. The individuals 210A-D sit in vehicles 215A-B. A first remote sensor 125 is attached to a drone 220 and a second and third remote sensors 125 are attached to the vehicles 215A-B. The drone 220 moves with the vehicles 215A-B so that the three remote sensors 125 are all in proximity to the individual. For example, the drone 220 receives an instruction specifying a direction and speed at which the vehicle 128 moves, and the drone 220 moves in the same direction at the same speed. Alternatively, the drone 220 detects movement of the vehicles 215A-B and moves in accordance with the detected movement of the vehicles 215A-B. In some embodiments, a remote sensor 125 may be attached to a satellite, aircraft, or other moving remote system.

In the embodiment of FIG. 2A, the remote sensors 125 are used to detect a blast 240 in an environment surrounding the vehicles 215A-B. In other embodiments, one of the remote sensors 125 is used. In one example, each of the remote sensors 125 includes an image sensor that collects light in the environment and captures image data of the environment. The image data includes information indicating the blast 240. A remote sensor 125 can collect light of visible or non-visible wavelengths (e.g., infrared wavelengths). The image can be sent to a controller (not shown in FIG. 2A). The controller may also be attached on the drone 220. An embodiment of the controller is the computing system 120. The controller uses the image data to determine whether the blast 240 will likely cause brain injury of an individual 210. In response to a determination that the blast 240 will likely cause brain injury, the controller sends an instruction to trigger an actuation device (examples shown in FIG. 5E and FIG. 5F) worn on the body of the individual 210. In one embodiment, the instruction is sent to the vehicle 215A or B of the individual and then forwarded to the actuation devices of the individual. In another embodiment, the instruction is first sent to the actuation device of a first individual 210 and then sent to the actuation device of a second individual 210 from the actuation device of the first individual 210. Also, the instruction can be sent to a first vehicle 215 from the controller and then sent to the other vehicle 215 from the first vehicle 215. Communications between the remote sensors 125, drone 220, controller, vehicles 215A-B, and actuation devices of the individuals 210A-D may be encrypted. A remote sensor 125 can be in communication (either direct or indirect) with the actuation device of an individual 210.

FIG. 2B shows a remote sensor 125 that is stationary, in accordance with an embodiment. FIG. 2B shows a playground 260 and a plurality of players 270 on the playground 260. The playground 260 can be other types of areas, such as a sports field, game location, a hospital, a nursing home, a building, a facility, and so on. A player 270 can be a patient in a hospital or nursing home, or other person in an environment where they were exposed to collisions, falls, impacts, or similar situations.

The remote sensor 125 is fixed on a corner of the playground 260. The remote sensor 125 also includes a tracking system that identifies players 270 and tracks one or more particular players 270 so that the remote sensor 125 can focus on a space surrounding the particular player(s) 270. The tracking system may be separate from the remote sensor 125. In the embodiment of FIG. 2B, the remote sensor 125 detects a collision 275A between the players 270A and 270B, a collision of the player 270C with the ground, or a collision of the player 270C with an object in a path of the player 270C. The collisions could cause sudden acceleration (or deceleration) of the brains of the players 270. Based on output from the remote sensor 125, a controller generates an instruction to activate actuation devices worn on the bodies of these players 270 (or any one of them). The actuation devices cause electrical stimulation to the neck and/or abdomen of the player to induce a gag reflex or a Valsalva-like maneuver. The gag reflex and Valsalva-like maneuver prevent brain injury that would otherwise result from the collision. FIG. 2B shows one remote sensor 125. Other embodiments can include multiple remote sensors 125 and/or tracking systems to make sure that at least one remote sensor 125 is in proximity to the wearable actuation device of every individual to be protected from brain injury.

In one embodiment, the remote sensors 125 may gather data in relation to the wearable device 155 of the brain injury reduction system 150. More specifically, the remote sensors 125 gather the position and orientation of the wearable device 155 prior, during, and subsequent to a collision which may cause head impact. Additionally, the remote sensors 125 gathers data corresponding to the collision which can include the speed of collision and estimated overall force imparted due to collision.

In various embodiments, the remote sensors 125 can gather data corresponding to multiple brain injury reduction systems 150. As a specific example, if the system environment 100 is employed for a football game, a first brain injury reduction system 150 can be associated with a first player and a second brain injury reduction system 150 can be associated with a second player. Therefore, the remote sensors 125 can track data corresponding to a collision between the first player and the second player. As an additional example, the remote sensors 125 can track the positions and/or speeds of the first player and the second player and detect an impending collision given their tracked positions and/or speeds.

In various embodiments, the remote sensors 125 can be in communication with the computing system 120. Therefore, the remote sensors 125 provide the gathered data corresponding to a wearable device 155 or the gathered data corresponding to a collision to the computing system 120 for analysis.

Example Computing System

A computing system 120 is in communication with the remote sensors 125 and one or more brain injury reduction systems 150 through the network 130. A computing system 120 may be a server computer, a client computer, a personal computer (PC), a tablet PC, a set-top box (STB), a smartphone, an internet of things (IoT) appliance, a network router, switch or bridge, or any machine capable of executing instructions (e.g., program code or software) stored in a memory that specify actions to be taken by that computing system 120.

In various embodiments, the computing system 120 receives data captured by one or both of the remote sensors 125 and data captured by the brain injury reduction system 150. The computing system 120 analyzes the data to improve upon the response to future collisions. As an example, the computing system 120 can more accurately determine whether a protective measure is needed. In some scenarios, a protective measure is needed when an individual is currently experiencing or will experience a collision that is unexpected. Alternatively, a protective measure is unneeded when an individual has anticipated an occurring collision or is anticipating for an impending collision.

In one embodiment, when a subsequent occurring or impending collision is detected, the computing system 120 receives data corresponding to that occurring or impending collision and determines whether a protective measure is needed. In other embodiments, the computing system 120 provides analysis information to the wearable device 155 such that when a subsequent occurring or impending collision is detected, the wearable device 155 can perform the analysis to determine whether a protective measure is needed.

After determining that a protective measure is needed, the computing system 120 generates an instruction to one or both of the actuation devices 160 and 165 to cause a Valsalva-like maneuver or a gag reflex of the user of the wearable device 150. The instruction can include a command to activate electrical stimulation to cause the Valsalva-like maneuver and/or gag reflex and can also include a command to stop the electrical stimulation. In one embodiment, the electrical stimulation can be performed by using transcutaneous electrodes that can cause glottis closure and/or electrodes that can cause abdominal muscle contraction. The instruction can also include one or more parameters for a cycle of electrical stimulation, such as amplitude (e.g., a voltage and/or current), frequency, a start time of the electrical stimulation, an end time of the electrical stimulation, and/or duration of the electrical stimulation. In some embodiments, the one or more parameters have values that do not exceed safety limits so that the electrical stimulation would be safe for the individual.

In some embodiments, the computing system 120 generates a calibration instruction for calibrating the actuation devices 160 and 165 before the cycle of electrical stimulation. The calibration instruction can include parameters for a series of electrical stimulations. After the actuation devices 160 and 165 conducts the calibration process based on the calibration instruction, the computing system 120 can receive calibration information indicating muscle condition of the individual, skin condition of the individual, or condition of the environment surrounding the individual, or other types of feedback information. The computer system 120 then generates the instruction for the cycle of electrical stimulation based on the calibration information.

In some embodiments, the computing system 120 also receives feedback from the wearable device 150 after the cycle of electrical stimulation. The feedback can include information indicating muscle fatigue of the user caused by a previous electrical stimulation. The feedback can also include information indicating effectiveness of a previous electrical stimulation, such as information indicating muscle contraction during the previous electrical stimulation or other types of effective indicator. The feedback can also include physiological parameters of the individual (such as sweating, activity load, etc.) and environmental parameters of the environment surrounding the individual (such as temperature, humidity, etc.). These parameters can be measured by sensors attached on the body of the individual and/or placed in the environment. The feedback can further include information indicating safety of previous electrical stimulations. The computing system 120 can store the feedback and use the feedback to generate an instruction for the next electrical stimulation. For example, the computing system 120 can determining a degree of muscle fatigue based on the feedback and determine amplitude, frequency, and/or duration of the next electrical stimulation based on the degree of muscle fatigue. Further discussion regarding the computing system 120 is described below in reference to FIG. 6.

Example Network

The network 130, which can be wired, wireless, or a combination thereof, enables communications between the brain injury reduction system 150, the computing system 120, and the remote sensors 125. The network 130 may include the Internet, a local area network (LAN), virtual LAN (VLAN) (e.g., with VPN), wide area network (WAN), or other network. In one embodiment, the network 130 uses standard communications technologies and/or protocols, such as Hypertext Transfer Protocol (HTTP), Transmission Control Protocol/Internet Protocol (TCP/IP), Uniform Resource Locators (URLs), and the Domain Name System (DNS). In another embodiment, the brain injury reduction system 150, the computing system 120, and the remote sensors 125 can use custom and/or dedicated data communications technologies (including encrypted communication technologies) instead of, or in addition to, the ones described above.

Example Wearable Device

Figure 2C:
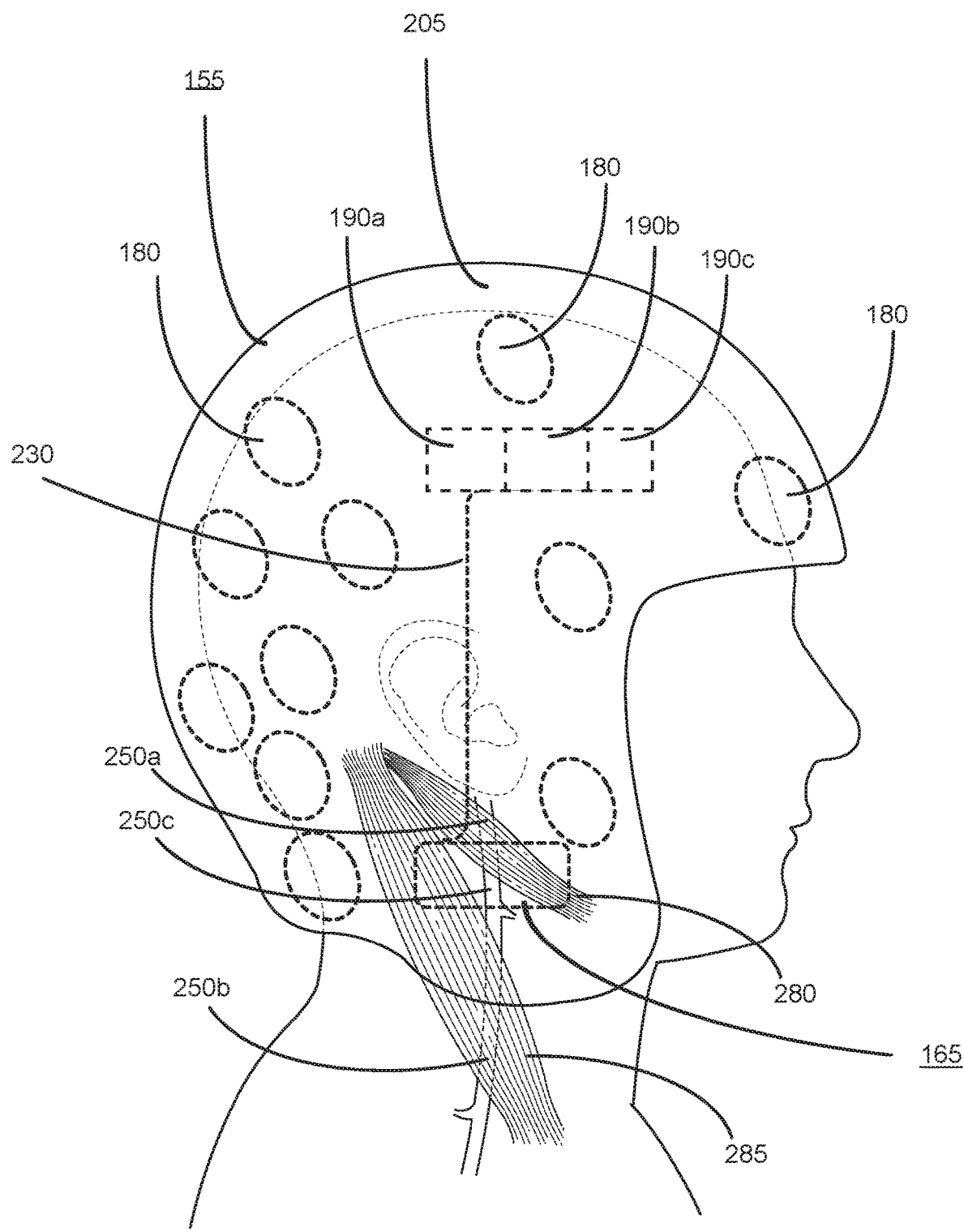
FIG. 2C illustrates a right side view of a wearable device in communication with an actuation device, in accordance with an embodiment.

FIG. 2C illustrates a right side view of a wearable device 155 in communication with an actuation device 2 (165), in accordance with an embodiment. The wearable device 155 can include sensors 180 and electronics 190. In some embodiments, the wearable device 155 includes wired connections 230 that enable the electronics 190 of the wearable device 155 to communicate with the actuation device 2 (165).

Referring to the sensors 180 of the wearable device 155, FIG. 2C depicts multiple sensors 180 distributed throughout the wearable device 155. In some embodiments, the sensors 180 are housed on or within a wearable housing 205 of the wearable device 155. For example, the wearable housing 205 may be the rigid helmet itself or a component within the rigid helmet. In various embodiments, the sensors 180 are evenly distributed or within the wearable housing 205 of the wearable device 155. In other embodiments, the concentration of sensors 180 at a location on or within the housing 205 of the wearable device 155 may be different where the individual may be more susceptible to brain injury. For example, as depicted in FIG. 2, the posterior of the wearable device 155 may include a higher concentration of sensors 180 in order to more accurately detect an occurring or impending collision that may be approaching from the posterior of a vulnerable individual.

The sensors 180 may be circular in shape. However, in various embodiments, the sensors 180 may be square, rectangular, triangular, oval, hexangular, or another polygon in shape. In some embodiments, the size of each sensor 180 can range from 1 millimeter to 5 centimeters or more in both size and thickness. In other embodiments, the size of the sensor 180 is larger and maintains its function of capturing a signal.

In one embodiment, the sensors 180 may be located on the external surface of the housing of the wearable device 155. In this scenario, the sensors 180 may be pressure sensors configured to detect changes in acoustics (e.g., pressure waves) in the vicinity of the sensors 180. As another example, the sensors 180 may be electromagnetic sensors configured to detect changes in electromagnetic radiation (e.g., energy across the electromagnetic spectrum such as light or magnetic waves) in the vicinity of the sensors 180. Generally, the changes in acoustics and/or changes in electromagnetic radiation may arise from an approaching object. Therefore, the sensors 180 on the external surface of the wearable device 155 can detect an impending collision due to the approaching object. In various embodiments, the sensors 180 detect an impending collision between 0 to 1 seconds beforehand. In some embodiments, the sensors 180 detect an impending collision between 100 to 500 milliseconds beforehand. In various embodiments, the sensors 180 detect an impending collision between 200 and 300 milliseconds beforehand.

In some embodiments, the sensors 180 may be located on an internal surface (e.g., on an inner most surface or within two layers) of the housing 205 of the wearable device 155. In this scenario, the sensors 180 may be one or both of accelerometers or gyroscopes that are configured to gather data regarding the orientation and/or position of the wearable device 155. An accelerometer can gather the linear kinematics (e.g., acceleration and velocity) along one or more axes of the wearable device 155 whereas the gyroscope can gather the rotational kinematics (e.g., acceleration and velocity) along one or more rotational axes of the wearable device 155.

In some embodiments, a wearable sensor 180 detects events in the environment surrounding an individual that may cause brain injury of the individual. For example, a wearable sensor 180 may be a sensor capable of capturing signals including, but not limited to, position, orientation, velocity, and acceleration of the body (or part of the body) of the individual. For example, a wearable sensor 180 may be a triaxial accelerometer that records acceleration data at that point relative to the earth in three dimensions. Such an acceleration sensor can be used to detect an impact or fall of the individual.

In various embodiments, a wearable device 155 can include sensors 180 located on both the external surface and the internal surface of the wearable device 155. For example, the wearable device 155 can include sensors 180 (e.g., pressure or electromagnetic sensors) configured to detect an impending collision from an approaching object as well as sensors 180 (e.g., accelerometer and gyroscope) configured to detect the orientation and/or position of the wearable device 155.

Referring now to the electronics 190 of the wearable device 155, the electronics 190 may include one or more of communication electronics 190a (e.g., that enable communication via Bluetooth, NFC, WiFi, 2G, 3G, 4G, or LTE), processor 190b, and power source 190c (e.g., battery). In various embodiments, the communication electronics 190a, the processor 190b, and power source 190c can be distributed at different locations around the wearable device 155. Each of the communication electronics 190a, processor 190b, and power source 190c can be housed within the housing 205 of the wearable device 155. Generally, the power source 190c provides power to the sensors 180, communication electronics 190a, and processor 190b of the wearable device 155.

Specifically, the communication electronics 190a enable the wearable device 155 to communicate with the remote sensors 125 and the computing system 120 through the network 130. Additionally, the communication electronics 190a enable the wearable device 155 to communicate with the actuation device 1 (160) and the actuation device 2 (165). Data communicated between these components can be digital data, analog data, or a combination of both.

In one embodiment, the communication electronics 190a of the wearable device 155 receives a trained machine-learning model to be applied by the processor 190b to determine whether a protective measure is required. In another embodiment, the communication electronics 190a of the wearable device 155 receives instructions from the computing system 120 indicating that a protective measure is required. Thus, the communication electronics 190a of the wearable device 155 can provide an input to one or both of the actuation device 1 (160) and the actuation device 2 (165) to transition from a rest state to an actuated state in order to reduce cerebral venous drainage from the individual's head. Additionally, the communication electronics 190a of the wearable device 155 can provide an input to one or both of the actuation device 1 (160) and the actuation device 2 (165) to cease actuation and transition back into a rest state.

In some embodiments, the wearable helmet 155 includes wired connections 230 such that the communication electronics 190a can directly communicate with actuation device 2 (165) through the wired connection 230. A wired connection 230 may be preferable to reduce the latency as compared to wireless communication methods.

Referring now to the processor 190b of the wearable helmet 155, in various embodiments, the processor 190b can be configured to execute instructions (e.g., code) that determine whether a protective measure is needed. Therefore, in this scenario, the processor 190b of the wearable helmet 155 receives a trained machine-learning model from the computing system 120 to be used to determine whether a protective measure is needed. For example, the processor 190b of the wearable helmet 155 can receive sensor-gathered data from the sensors 180 of the wearable helmet 155 and apply the sensor-gathered data as input to the trained machine-learning model. More specifically, the trained machine-learning model analyzes the sensor data (e.g., orientation and/or position of the wearable helmet 155 and/or impending collision information) and outputs whether the protective measure is to be performed. As an example, the machine-learning model may be trained to classify impending collisions that a vulnerable individual is not expecting (e.g., from the posterior of the individual) as requiring a protective measure. Therefore, if a protective measure is deemed necessary by the machine learning model, the processor 190*b* instructs the communication electronics 190*a* to transmit inputs to actuate one or both of actuation device 1 (160) and actuation device 2 (165).

In various embodiments, the processor 190*b* further detects an endpoint and subsequently instructs the communication electronics 190*a* to provide an input to one or both of actuation device 1 (160) and actuation device 2 (165) to transition from an actuated state back to the rest state. Therefore, the individual that was provided the protective measure need not experience prolonged physical compression on the IJV and/or a prolonged induced gag reflex and/or Valsalva-like maneuver.

In various embodiments, the detected endpoint may be a collision. For example, a preventive measure can initially be provided in response to an impending collision. Once the impending collision is detected or estimated, the processor 190*b* detects the occurred collision as an endpoint and provides input such that the actuation device 1 (160) and/or actuation device 2 (165) transitions back to the rest state. In some embodiments, the endpoint is the detection of multiple collisions. For example, a first collision may correspond to a collision with a moving object (e.g., a collision with another football player) whereas a second collision may correspond to a collision with an inanimate object (e.g., the ground). Therefore, the protective measure may be held and provided through the multiple collisions. Once the processor 190*b* receives notification that multiple collisions were detected, the processor 190*b* can provide input to transition the actuation device 1 (160) and/or actuation device 2 (165) back to the rest state. In some embodiments, the detected endpoint is a threshold duration of time. For example, the duration may be several seconds (e.g., 3 seconds, 5 seconds, or 10 seconds). After the threshold duration of time has passed, the processor 190*b* causes the actuation device 1 (160) and/or actuation device 2 (165) to transition back to the rest state.

Example Actuation Device for Closing Internal Jugular Veins

Referring to FIG. 2, the actuation device 2 (165) may be located on the interior of the housing 205 wearable device 155. Specifically, the actuation device 2 (165) is located between the wearable device 155 and the skin of the individual that is external to the jugular veins. In some embodiments, the actuation device 2 (165) is configured to compress one or both of the left/right internal jugular veins (IJV) and the external jugular veins (EJV). Although FIG. 2C depicts a right side view of the actuation device 2 (165) that is configured to externally compress the one or both of the right IJV and right EJV, one skilled in the art can readily understand that the actuation device 2 (165) can be configured to provide bilateral compression to both the right and left IJV/EJV. Therefore, the subsequent description refers to both the right and left IJV/EJV.

FIG. 2C further depicts the anatomical structure of the right IJV of the human individual. Specifically, the digastric muscle 280 is positioned superficially relative to a first portion 250*a* of the IJV. In other words, the digastric muscle 280 covers and prevents external access through the skin to the first portion 250*a* of the IJV. Additionally, the sternocleidomastoid muscle 285 is positioned superficially relative to a second portion 250*b* of the IJV. In other words, the sternocleidomastoid muscle 285 covers and prevents external access through the skin to the second portion 250*b* of the IJV. As shown in FIG. 2, the first portion 250*a* of the IJV is proximal to the individual's brain relative to the second portion 250*b* of the IJV. A third portion 250*c* of the IJV is externally accessible by compression through the skin. Therefore, the actuation device 2 (165) can be in contact with the skin of the individual located external to the third portion 250*c* of the IJV such that the actuation device 2 (165), when actuated, physically compresses and reduces cerebral venous drainage through the IJV.

Figure 3A:
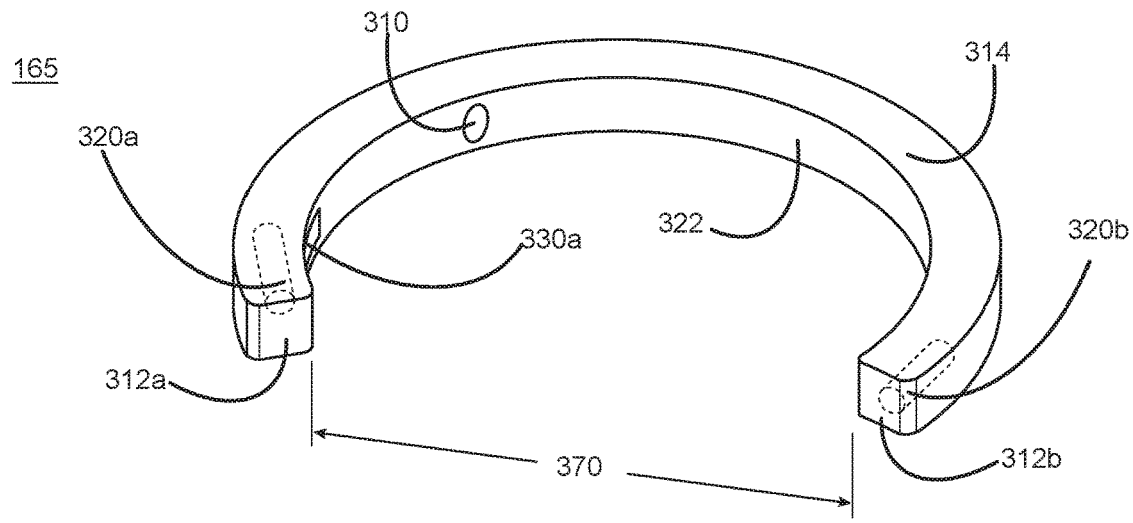
FIGS. 3A-C illustrates an example actuation device for compressing the jugular veins of an individual, in accordance with an embodiment.
Figure 3B:
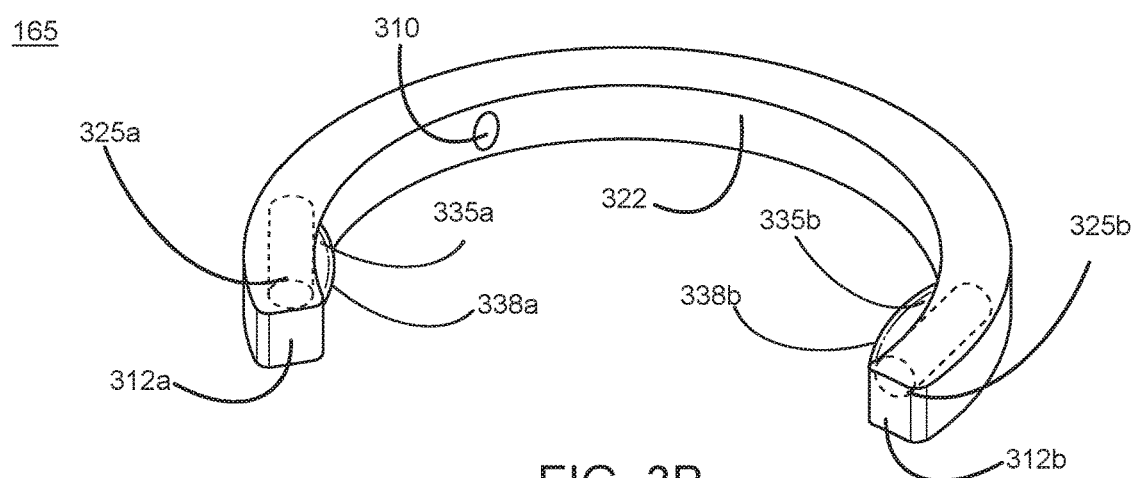
Figure 3C:
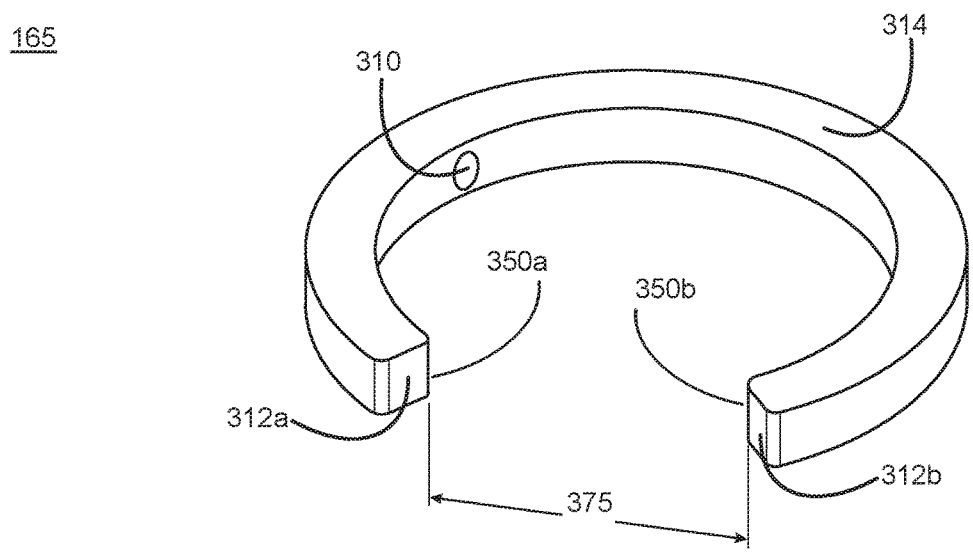

Reference is now made to FIGS. 3A-3C, which each illustrates an example actuation device 2 (165) for compressing the IJVs of an individual, in accordance with an embodiment. More specifically, FIG. 3A depicts the actuation device 2 (165) in a rest state. The actuation device 2 (165) may be composed of a body, otherwise referred to as the housing 314. The housing 314 may include a first end 312*a* and a second end 312*b*. The actuation device 2 (165) includes communication electronics 310 that enable the actuation device 2 (165) to communicate with the wearable device 155 through one of Bluetooth, near field communication (NFC), WiFi, 2G, 3G, 4G, LTE, or other wireless or wired communication methods. In some embodiments, the actuation device 2 (165) further includes stimulation structures. In FIG. 3A, these stimulation structures include an extendable structure 330*a* located on an inner surface 322 of the housing 314 of the actuation device 2 (165) near the first end 312*a*. Of note, the actuation device 2 (165) may also include an extendable structure located on an inner surface 322 of the housing 314 of the actuation device 2 (165) near the second end 312*b* which is not shown in FIG. 3A. Additionally, the actuation device 2 (165) can include one or more actuating components 320.

Referring first to the communication electronics 310 of the actuation device 2 (165), they enable the actuation device 2 (165) to communicate with the wearable device 155. Specifically, the communication electronics 310 of the actuation device 2 (165) receives input from the wearable device 155 after a protective measure is deemed necessary. Therefore, the actuation device 2 (165) can transition from a rest state, as depicted in FIG. 3A, to an actuated state as is depicted in FIGS. 3B and 3C. Alternatively, the communication electronics 310 can receive input from the wearable device 155 after an endpoint is detected. Therefore, the actuation device 2 (165) can transition from the actuated state back to the rest state. Although FIG. 3A depicts the communication electronics 310 as being located on the inner surface 322 of the housing 314 of the actuation device 2 (165), in various embodiments, the communication electronics 310 can be located on another surface of the housing 314 or internally within the housing 314 of the actuation device 2 (165).

In various embodiments, the housing 314 and the extendable structures 330 of the actuation device 2 (165) are each constructed from a solid polymer including, but not limited to, polystyrene, polypropylene, polyurethane, nylon, leather, rubber, and the like. Therefore, any component of the actuation device 2 (165), and more specifically the extendable protrusions 330, that contact the individual would retain its structure, thereby enabling the actuation device 2 (165) to physically compress the IJVs.

The actuation device 2 (165) may have dimensional characteristics that are tailored for the individual that wears the actuation device 2 (165). Specifically, the first end 312*a* and the second end 312*b* of the actuation device 2 (165) may be a pre-determined distance 370 apart. The pre-determined distance 370 can be selected according to the anatomical characteristics of the individual (e.g., neck size of the individual). Additionally, the housing 314 of the actuation device 2 (165) may have a curvature that is also selected according to the anatomical characteristics of the individual. For example, the curvature of the housing 314 can be designed to allow for about a 1 centimeter gap between actuation device 2 (165) and the neck of the individual when the actuation device 2 (165) is in a rest position. In other embodiments, the curvature of the housing 314 is designed to allow, for example, for a gap anywhere from 0.1 mm to 100 mm between actuation device 2 (165) and the neck of the individual when the actuation device 2 (165) is in a rest position. As such, the actuation device 2 (165) need not contact the skin of the individual in the rest position until a protective measure is determined to be required, which can trigger the actuation device 2 (165) to transition into the actuated state. Generally, the pre-determined distance 370 and the curvature of the housing 314 are selected such that the internal surface 322 of the actuation device 2 (165) remains a distance away from the skin of the individual when the actuation device 2 (165) is in the rest state. In some embodiments the internal surface 322 of the actuation device (165) may rest on the skin of the individual.

As described above, the housing 314 of the actuation device 2 (165) may include a first extendable protrusion 330a and a second extendable protrusion 330b on an internal surface 322 of the actuation device 2 (165). Additionally, the housing 314 of the actuation device 2 (165) can further house multiple actuating components 320. In some embodiments, each actuating component 320 is located within the actuation device 2 (165) as is indicated by the dotted outline structure in FIG. 3A. In various embodiments, the housing 314 may only include a single actuating component 320 that is configured to trigger both extendable protrusions 330a and 330b.

In the rest state, each extendable protrusion 330 can sit flush with the internal surface of the actuation device 2 (165). Therefore, in the rest state, each extendable protrusion 330 is unlikely to unintentionally contact the individual's skin and the underlying IJV. Each extendable protrusion 330 can transition from a rest state (e.g., flush to the inner surface 322) to an actuated state (e.g., extended outward from the inner surface 322) due to actuating components 320 of the actuation device 2 (165).

Each actuating component 320 of the actuation device 2 (165) can be triggered when the communication electronics 310 of the actuation device 2 (165) receives the input indicating a need for a protective measure from the wearable device 155. As shown in FIG. 3A, the actuation device 2 (165) includes two actuating components 320. A first actuating component 320a can be located within the housing 314 near or at the first end 312a whereas the second actuating component 320b can be located within the housing 314 near or at the second end 312b.

An actuating component 320 can provide one of a mechanical, chemical, or electrical inputs to cause an extendable protrusion 330 to change its configuration. This may occur in response to the communication electronics 310 receiving an input from the wearable device 155. For example, the actuating component 320 may be a physical structure that displaces inward. As such, the actuating component 320 mechanically displaces the extendable protrusion 330 to protrude inward from the inner surface 322. As another example, the actuating component 320 may store expandable fluids in separate compartments or cartridges such as gasses, liquids, gels, and the like. Thus, the expandable fluids can be mixed when desired that causes an increase in volume. The increase in volume can cause the extendable protrusions 330 to change their configuration and protrude inward from the inner surface 322. As another example, the actuating component 320 may include electrical components that provide an electrical input that cause the extendable protrusions 330 to change their configuration.

FIG. 3B depicts one embodiment of the actuation device 2 (165) in an actuated state. Specifically, each actuating component 325a and 325b may now be in an actuated state, as indicated by their larger size in FIG. 3B as compared to their counterparts 320a and 320b shown in FIG. 3A. Each actuated actuating component 325 causes a corresponding change to achieve an extended protrusion 335a and 335b. For example, each extended protrusion 335 is extended inward from the inner surface 322 when in an actuated state. Therefore, the first extended protrusion 335a can physically compress the right EJV and/or IJV whereas the second extended protrusion 335b can physically compress the left EJV and/or IJV. In some embodiments, the actuation device 2 (165) can have two extended protrusions 335 on either side (total of four extended protrusions 335), each extended protrusion configured to physically compress one of the right EJV, right IJV, left EJV, and left IJV.

As shown in FIG. 3B, each extended protrusion 335 may possess a convex rounded edge 338 that extends inward from the inner surface 322. As such, the rounded edge 338 of the extended protrusion 335 physically compresses the EJV and/or IJV of the individual. In other embodiments, the extended protrusion 335 may have other configurations such as a square, rectangular, or other polygonal shapes that may enable the extended protrusion 335 to focally compress the EJV and/or IJV of the individual.

In various embodiments, when the actuation device 2 (165) is in the actuated state, the distance between the first end 312a and the second end 312b remains unchanged in comparison to the distance when the actuation device 2 (165) is in the rest state. In some embodiments, as is shown in FIG. 3C, the distance 375 between the first end 312a and the second end 312b decreases when the actuation device 2 (165) transitions to the actuated state.

In this embodiment, the housing 314 may be composed of a flexible material. As such, when transitioning from the rest state to the actuated state, the housing 314 of the actuation device 2 (165) can reduce its curvature such that the reduced distance 375 between the first end 312a and the second end 312b is decreased compared to the distance 370 shown in FIG. 3A. In some embodiments, the flexible material is an electroactive polymer such as a liquid crystalline polymer, or a piezoelectric polymer.

As shown in FIG. 3C, the actuation device 2 (165) need not include extendable protrusions 330 as was shown in FIGS. 3A and 3B. In various embodiments, the first end 312a and the second end 312b each have vertical edges 350a and 350b, respectively. The vertical edges 350 of each of the first end 312a and second end 312b can physically contact the skin of the individual, thereby bilaterally compressing the IJV of the individual.

Example Device for Stimulating a Gag Reflex

Figure 4A:
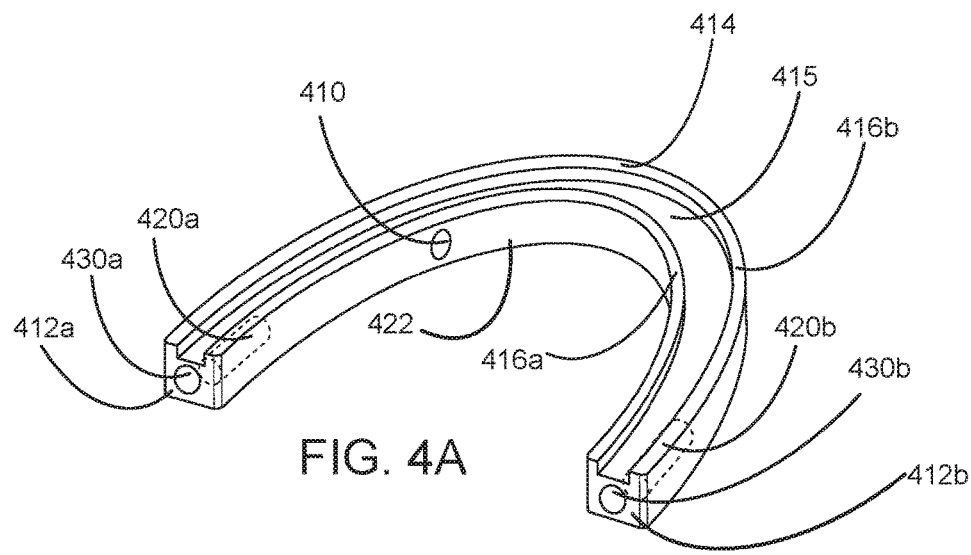
FIGS. 4A-4C each illustrates an example actuation device for inducing a gag reflex in an individual, in accordance with an embodiment.
Figure 4B:
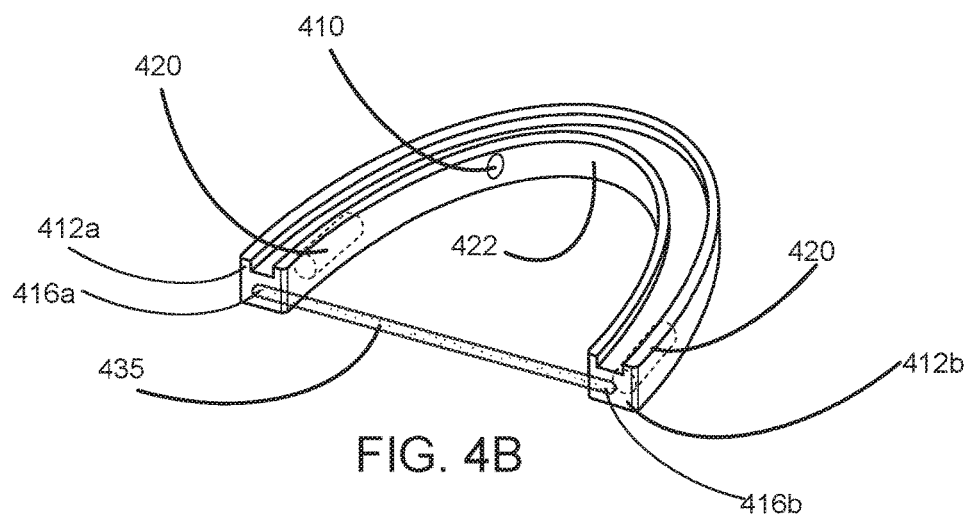
Figure 4C:
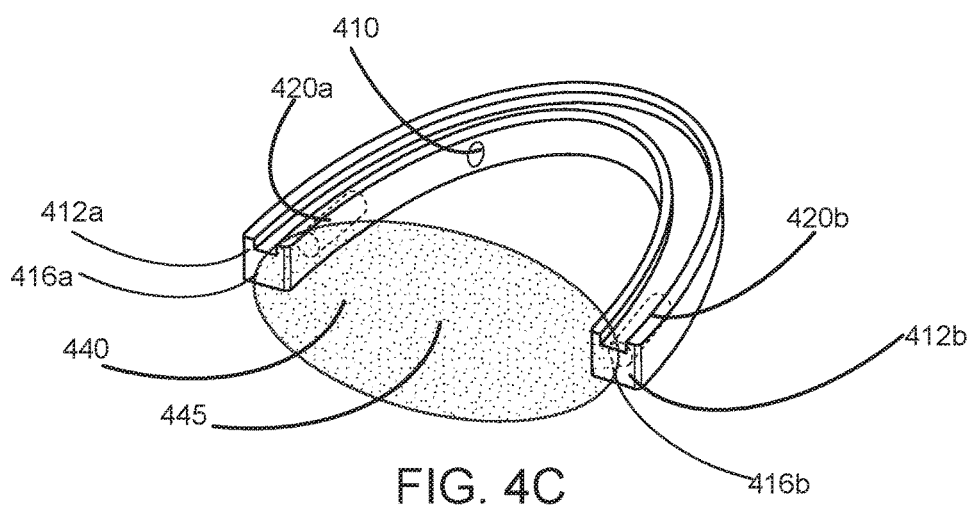

FIGS. 4A-C each illustrates an example actuation device 160 for inducing a gag reflex in an individual, in accordance with an embodiment. In one embodiment, a gag reflex can be invoked by the actuation device 1 (160) by physically contacting the actuation device 1 (160) with one or more various locations within the individual's mouth. For example, the stimulation structures of the actuation device 1 (160) may contact the back of the tongue, at or around the tonsils, the uvula, or the back of the throat. The physical contact can result in stimulation of the glossopharyngeal nerve, thereby resulting in a gag reflex. In other embodiments, a gag reflex can be invoked by the actuation device 1 (160) by directly electrically stimulating a nerve, such as the glossopharyngeal nerve, to cause the gag reflex.

Specifically, FIG. 4A depicts the actuation device 1 (160) in a rest state. The actuation device 1 (160) may be configured to be worn in a mouth of the individual. For example, as depicted in FIG. 4A, the actuation device 1 (160), is designed as a mouthguard device configured to reside within the mouth of the individual. Specifically, the actuation device 1 (160) may include a housing 414 that further includes a first end 412a and a second end 412b. The housing 414 may be contoured (e.g. curved) and may include features such as an inner ridge 416a, and outer ridge 416b, and a cavity 415 formed by the inner ridge 416a and outer ridge 416b. Additionally, the actuation device 1 (160) can include communication electronics 410, actuating components 420, and stimulation structures 430.

Referring first to the housing 414 of the actuation device 1 (160), as depicted in FIG. 4A, the housing 414 includes the inner ridge 416a and the outer ridge 416b. The inner ridge 416a forms the internal surface 422 of the actuation device 1 (160) and connects the first end 412a of the housing 414 to the second end 412b of the housing 414. The outer ridge 416b forms an external surface of the actuation device 1 (160) and similarly connects the first end 412a of the housing 414 to the second end 412b of the housing 414. A cavity 415 can be located between the inner ridge 416a and the outer ridge 416b. In other words, the cavity 415 is lined on either side by one of the inner ridge 416a or the outer ridge 416b. In some embodiments, the cavity 415 has a depth between 1 millimeter and 20 millimeters. Specifically, the depth of the cavity 415 can be designed such that the individual's teeth can comfortably reside in the cavity 415 when the actuation device 1 (160) is worn in the mouth. Furthermore, the cavity 415 (as well as the inner ridge 416a and outer ridge 416b) is shaped with a particular curvature. In various embodiments, the curvature may be determined based on the curvature of the individual's teeth.

As depicted in FIG. 4A, the cavity 415 is located on a top side of the actuation device 1 (160) and therefore, enables an individual's upper teeth to rest comfortably in the cavity 415 when the actuation device 1 (160) is worn. In various embodiments, the actuation device 1 (160) further includes a cavity (not shown) on the underside of the actuation device 1 (160). The cavity on the underside of the actuation device 1 (160) may be similarly configured as the cavity 415 on the top side of the actuation device 1 (160). As such, the cavity on the underside of the actuation device 1 (160) may similarly enable an individual's lower teeth to rest comfortably in the cavity when wearing the actuation device 1 (160). In some embodiments, the cavity 415 on either the top or underside of the actuation device 1 (160) includes additional features such as undulations or indentations that are designed to mimic the shape (e.g., gaps, indentations and the like) of the individual's upper or lower teeth.

Referring to the communication electronics 410 of the actuation device 1 (160), they enable the actuation device 1 (160) to communicate with the wearable device 155 through one of Bluetooth, near field communication (NFC), WiFi, 2G, 3G, 4G, LTE, or other wireless or wired communication methods. Specifically, the communication electronics 410 of the actuation device 1 (160) receives input from the wearable device 155 after a protective measure is deemed necessary. Therefore, the actuation device 1 (160) can transition from a rest state, as depicted in FIG. 4A, to an actuated state as is depicted in FIGS. 4B and 4C. Alternatively, the communication electronics 410 can receive input from the wearable device 155 after an endpoint is detected. Therefore, the actuation device 1 (160) can transition from the actuated state back to the rest state. Although FIG. 4A depicts the communication electronics 410 as being located on the inner surface 422 of the actuation device 1 (160), in various embodiments, the communication electronics 410 can be located on another surface or internally within the housing 414 of the actuation device 1 (160).

The actuation device 1 (160) can include multiple actuating components 420a and 420b that are triggered when the communication electronics 410 of the actuation device 1 (160) receives the input indicating a need for a protective measure from the wearable device 155. As shown in FIG. 4A, a first actuating component 420a can be located in the housing 414 near or at the first end 412a whereas a second actuating component 420b can be located in the housing 414 near or at the second end 412b. In other embodiments, the actuating components 420 can be located within the housing 414 of the actuation device 1 (160) at other locations.

An actuating component 420 of the actuation device 1 (160) can provide one of a mechanical, chemical, or electrical inputs to actuate a stimulation structure 430. In other embodiments, input can be of a different energy modality such as an electromagnetic (e.g., magnetic) input. Specifically, in the embodiment shown in FIG. 4A, the actuating component 420 can provide an electrical input through the stimulation structure, also referred to as the electrodes 430. A first electrode 430a can be located at the first end 412a whereas a second electrode 430b can be located at the second end 412b. The electrodes 430 may be electrical contacts on a surface of the first end 412a and a surface of the second end 412b. Therefore, when actuated, an actuating component 420 can provide an input through the electrical contacts of the electrodes 430 in order to cause a gag reflex. Specifically, in reference to FIG. 4A, the actuating component 420 can be electrical hardware (e.g., battery, circuitry hardware) configured to provide an electrical input. The electrical contacts of the electrodes 430 can provide the electrical input (an applied voltage or an applied current) to the individual wearing the actuation device 1 (160).

In various embodiments, when residing in the mouth of the individual, the first end 412a and the second end 412b of the actuation device 1 (160) may each be in contact with a portion of the mouth of the individual. Specifically, the first end 412a and the second end 412b of the actuation device 1 (160) are in contact with one of the back of the tongue, the tonsils or areas around the tonsils, the uvula, or the back of the throat. Therefore, the electrode contacts of the electrodes 430 can similarly be in contact with one of the back of the tongue, the tonsils or areas around the tonsils, the uvula, or the back of the throat. The electrical input applied by the electrode 430 can trigger the glossopharyngeal nerve at the back of the individual's mouth to cause the gag reflex.

In various embodiments, the actuation device 1 (160) imparts a bilateral electrical stimulation through the two electrode contacts of the two electrodes 430. In some embodiments, a unilateral stimulation through a single electrode contact of a single electrode 430 is sufficient to cause a corresponding gag reflex in the individual.

Reference is now made to FIG. 4B, which illustrates a different embodiment of the actuation device 1 (160) for stimulating a gag reflex. Specifically, as shown in FIG. 4B, the actuation device 1 (160) is in a rest state. In this embodiment, the stimulation structure of the actuation device 1 (160) may be an inflatable structure 435 that causes a gag reflex in the individual. In various embodiments, this embodiment does not include electrode contacts of electrodes 430 as shown in FIG. 4A. In some embodiments, both the electrode contacts of the electrodes 430 and an inflatable structure 435 are included in the actuation device 1 (160) for stimulating a gag reflex.

The inflatable structure 435 may be coupled to the first end 412a of the actuation device 1 (160) through a first attachment point 416a. Furthermore, the inflatable structure 435 can be coupled to the second end 412b of the actuation device 1 (160) through a second attachment point 416b. Therefore, as shown in FIG. 4B, the inflatable structure 435 may directly traverse the distance between the first end 412a and the second end 412b of the actuation device 1 (160). In some embodiments, when in the rest state, the inflatable structure 435 can traverse along the inner surface 422 of the actuation device 1 (160). In other words, the inflatable structure 435 may follow the curvature of the inner surface 422 of the actuation device 1 (160) such that the inflatable structure 435 is less than a threshold distance away from the inner surface 422. Here, positioning the inflatable structure 435 close the inner surface 422 of the actuation device 1 (160) can prevent accidental stimulation of a gag reflex.

In various embodiments, the actuation device 1 (160) may include more than one inflatable structures 435. For example, a first inflatable structure 435 can be coupled at the first attachment point 416a to the first end 412a of the housing 414. Additionally, a second inflatable structure 435 can be coupled at the second attachment point 416b to the second end 412b of the housing 414. In some embodiments, when in the rest state, each of the first and second inflatable structure 435 may sit flush with the surface of the first end 412a and the surface of the second end 412b. For example, the first and second inflatable structure 435 can be stored in a cavity in the first end 412a and the second end 412b, respectively. Thus, this can prevent accidental stimulation of a gag reflex by the inflatable structures 435 when in a rest state.

FIG. 4C depicts the actuation device 1 (160) in an actuated state, in accordance with an embodiment. Here, the inflatable structure 435 shown in FIG. 4B changes its configuration to achieve an actuated inflated structure 440 (e.g., inflated). The actuated inflated structure 440 may remain coupled through the first attachment point 416a to the first end 412a of the housing 414 and through the second attachment point 416b to the second end 412b of the housing 414. When worn in the mouth of the individual, the actuated inflated structure 440 can physically contact one of the back of the tongue, the tonsils or areas around the tonsils, the uvula, or the back of the throat. As such, the actuated inflated structure 440 causes a gag reflex to occur in the individual.

In this embodiment, to achieve the actuated state, the actuating components 420 of the actuation device 1 (160) can cause the transition from the inflatable structure 435 shown in FIG. 4B to the actuated inflated structure 440 shown in FIG. 4C. As described above, the actuating components 420 can provide a chemical input. For example, each actuating component 420 can be configured to mix substances such as gasses, liquids, gels, and the like. Each substance can be stored within a cartridge that may be internal to the actuation device 1(160) or external to actuation device 1 (160). Mixing the substances causes a conversion of the substances into an expanded fluid, gas, or vapor that subsequently fills the inflatable structure 435. Altogether, the mixing of substances generates an expanded fluid, gas, or vapor that actuates (e.g., inflates) the inflatable structure 435 to achieve the actuated inflated structure 440 shown in FIG. 4C.

In some embodiments, the first actuating component 420a actuates a first inflatable structure 435 coupled to the first end 412a through attachment point 416a. Additionally, the second actuating component 420b actuates a second inflatable structure 435 coupled to the second end 412b through attachment point 416b. Therefore, the two inflatable structures may each actuate (e.g., inflate) and cause a gag reflex.

In various embodiments, the actuated inflated structure 440 (and the inflatable structure 435 when at rest) include vents 445 distributed throughout the actuated inflated structure 440 that enables a substance from within the actuated inflated structure 440 to escape. For example, the expanded fluid, gas, or vapor that actuated the inflatable structure 435 can escape through the vents 445 at a controlled rate depending on the size of the vents 445. As such, the actuated inflated structure 440 can return from the actuated state back to the inflatable structure 435 at a rest state. In another embodiment, the actuated inflated structure 440 includes a vent 445 that can be opened or closed given an electrical, chemical, or mechanical input. The input can be provided by the actuating component 420. As such, when the wearable device 155 detects that a protective measure is needed, the vent 445 can be closed when transitioning the actuation device 1 (160) from a rest state to an actuated state. Likewise, when the wearable device 155 detects an endpoint, vent 445 can be opened to transition the actuation device 1 (160) from an actuated state to a rest state.

Example Device for Stimulating a Valsalva-like Maneuver

Figure 5A:
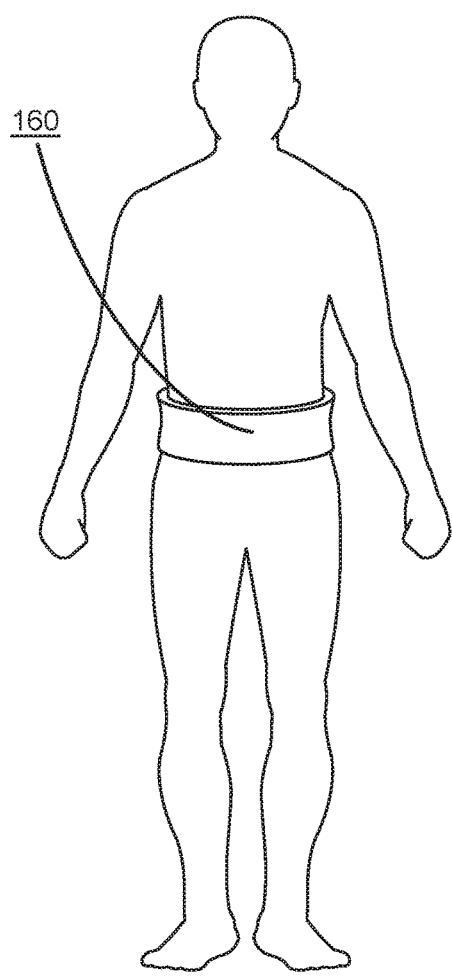
FIGS. 5A-5I illustrate examples of actuation devices for inducing a Valsalva-like maneuver, in accordance with an embodiment.
Figure 5B:
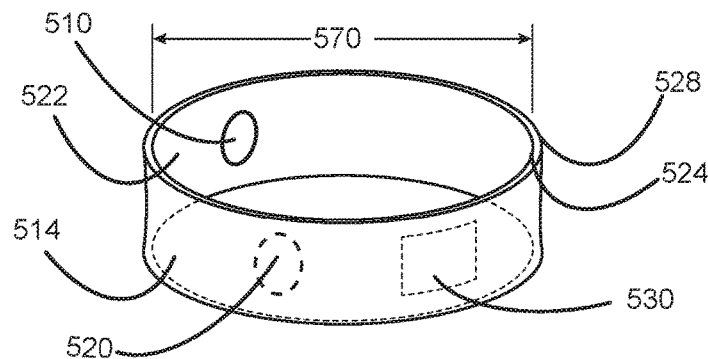
Figure 5C:
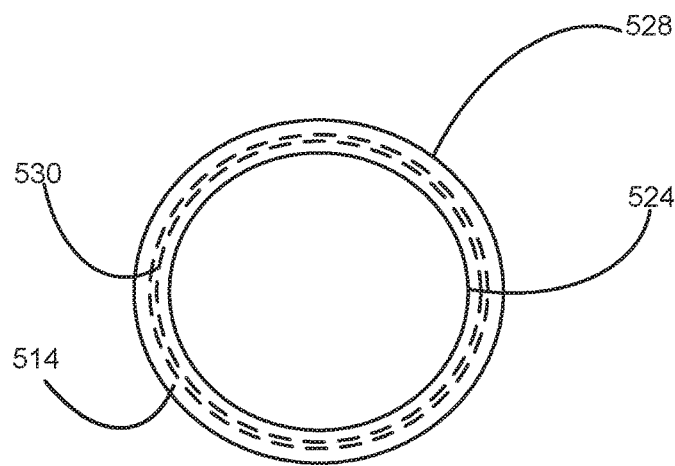

FIGS. 5A-C illustrates an example actuation device 1 (160) for inducing a Valsalva-like maneuver, in accordance with an embodiment. For example, as depicted in FIG. 5A, the example actuation device 1 (160) is a waistband worn by an individual around his/her waist. In this embodiment, the waistband can be situated external to the individual's diaphragm. As such, when actuated, the waistband causes a Valsalva-like maneuver by compressing the diaphragm and causing an increase in intraabdominal pressure and pressure within the thoracic cavity. In other embodiments, the example actuation device 1 (160) can be worn at any anatomical region between the chest and the waist. Although FIG. 5A depicts the waistband as fully encircling the individual's waist, in some embodiments, the waistband only encircles a portion of the individual. In some embodiments, the waistband encircles less than 50% of the individual's waist.

Referring to FIG. 5B, the actuation device 1 (160) may include communication electronics 510 and an actuating component 520 located within a housing 514 of the actuation device 1 (160). The actuation device 1 (160) may have an inner wall 524 and an outer wall 528. As such, the actuation device 1 (160) has inner diameter 570. Additionally, between the inner wall 524 and outer wall 528, the actuation device 1 (160) can include a stimulation structure such as an expandable cavity 530.

Figure 5D:
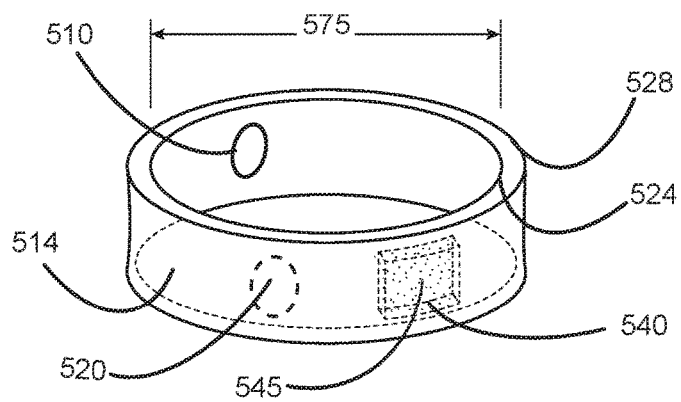

Similar to the communication electronics 410 described above in regards to FIG. 4, the communication electronics 510 of the actuation device 1 (160) can enable the actuation device 1 (160) to communicate with the wearable device 155 through one of Bluetooth, near field communication (NFC), WiFi, 2G, 3G, 4G, LTE, or other wireless or wired communication methods. Specifically, the communication electronics 510 of the actuation device 1 (160) receives input from the wearable device 155 after a protective measure is deemed necessary. Therefore, the actuation device 1 (160) can transition from a rest state, as depicted in FIG. 5B, to an actuated state as is depicted in FIG. 5D. Alternatively, the communication electronics 510 can receive input from the wearable device 155 after an endpoint is detected. Therefore, the actuation device 1 (160) can transition from the actuated state back to the rest state. In various embodiments, the communication electronics 510 can be located on the inner surface 522 of the actuation device 1 (160). In various embodiments, the communication electronics 510 can be located internally within the actuation device 1 (160).

The dimensions of the actuation device 1 (160) can be configured such that the actuation device 1 (160) be comfortably worn at the individual's waist when in the rest state. For example, the inner diameter 570 is designed so the inner wall 524 of the actuation device 1 (160) contacts, but does not constrict, the individual's waist. In various embodiments, the distance between the inner wall 524 and the outer wall 528 of the actuation device 1 (160) can range from 1 centimeter up to 10 centimeters when in the rest state.

The stimulation structure of the actuation device 1 (160), specifically an expandable cavity 530 as shown in FIG. 5B, is located between the inner wall 524 and the outer wall 528 of the actuation device 1 (160). In one embodiment, the expandable cavity 530 is only located within a portion of the actuation device 1 (160). As shown in FIG. 5B, the expandable cavity 530 may be a cavity that, when worn by the individual, is situated externally to the diaphragm. Therefore, actuation of the expandable cavity 530 would directly compress the diaphragm and cause a Valsalva-like maneuver. FIG. 5C depicts a top-down view of another embodiment of the expandable cavity 530, as indicated by the dotted outlined structure, within the actuation device 1 (160) in the rest state. In this scenario, the expandable cavity 530 is concentrically located between the inner walls 524 and the outer walls 528 of the actuation device 1 (160).

Referring back to FIG. 5B, the actuating component 520 can cause the expandable cavity 530 to actuate (e.g., expand). As described above, the actuating component 520 can provide one or more of a mechanical, chemical, or electrical input to actuate the expandable cavity 530. As an example, each actuating component 530 can mix substances such as gasses, liquids, gels, and the like. The substances can be initially stored in a cartridge that is internal or external to the actuating device 1 (160). Mixing the substances causes a conversion of the substances into an expanded fluid, gas, or vapor that subsequently fills and expands the expandable cavity 530. The expansion of the expandable cavity 530 can happen in an instantaneous manner (e.g., less than 1 second). As such, the expandable cavity 530 can be actuated, as depicted in FIG. 5D.

FIG. 5D depicts the actuation device 1 (160) in an actuated state, in accordance with an embodiment. Generally, the actuated cavity 540 can cause the actuation device 1 (160) to alter its configuration and cause a Valsalva-like maneuver. The distance between the inner wall 524 and the outer wall 528 can be increased in the actuated state as compared to the corresponding distance when in the rest state. Additionally, the inner diameter 575 of the actuation device 1 (160) can be reduced in the actuated state as compared to the inner diameter 570 of the actuation device 1 (160) when in the rest state. Although FIG. 5C depicts a reduced inner diameter 575 across the entire inner wall 524, in various embodiments, a reduced inner diameter 575 only occurs in a portion of the actuation device 1 (160). For example, if the expandable cavity 530 is within a portion of the actuation device 1 (160) as shown in FIG. 5B, then the reduced inner diameter 575 of the actuation device 1 (160) can correspond to the location of the inner wall 524 where the actuated cavity 540 is located.

In various embodiments, the actuated cavity 540 also include vents 545 distributed throughout the actuated cavity 540. The vents 545 may be connected through the inner wall 524 or outer wall 528 such that a substance from within the actuated cavity 540 can escape out to the environment. For example, the expanded fluid, gas, or vapor that previously actuated the expandable cavity 530 can escape through the vents 545 at a controlled rate depending on the size of the vents 545. As such, the actuated cavity 540 can return from the actuated state back to the expandable cavity 530 at a rest state. In another embodiment, the actuated cavity 540 includes a vent 545 that can be opened or closed given an electrical, chemical, or mechanical input. The input can be provided by the actuating component 520. As such, when the wearable device 155 detects that a protective measure is needed, the vent 545 can be closed when transitioning the actuation device 1 (160) from a rest state to an actuated state. Likewise, when the wearable device 155 detects an endpoint, vent 545 can be opened to transition the actuation device 1 (160) from an actuated state to a rest state.

Figure 5E:
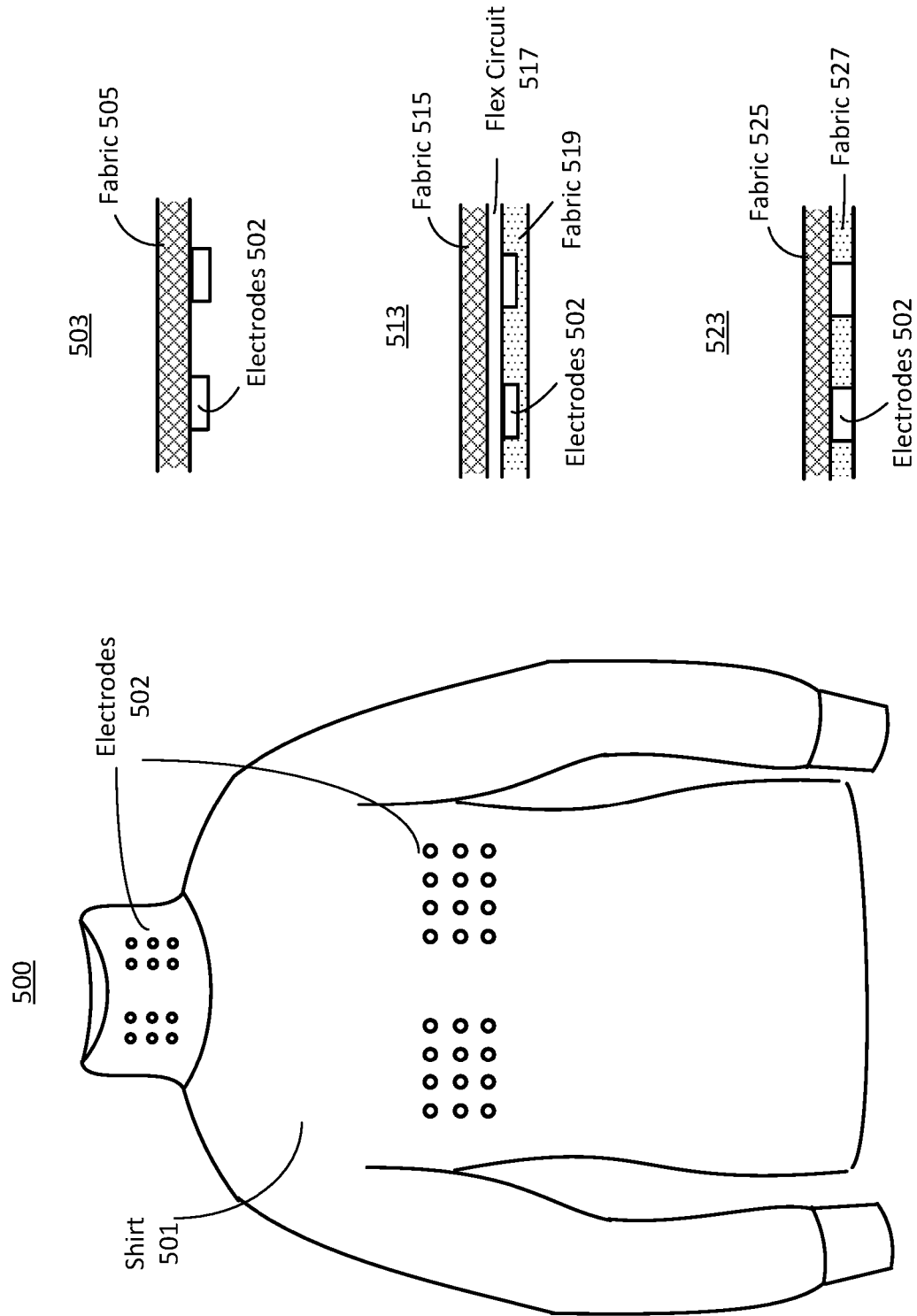

The Valsalva-like maneuver or gag reflex can also be electrically simulated. FIG. 5E illustrates an example actuation device 500 configured to cause electrical stimulation to induce a Valsalva-like maneuver and/or a gag reflex, in accordance with one embodiment. The actuation 500 can be an alternative to the actuation system 1 (160) and the actuation system 2 (165) in FIG. 1A. The actuation device 500 applies electrical stimulation to the neck and/or abdomen of the individual to induce glottis closure and/or contraction of the abdominal musculature to cause a Valsalva-like maneuver. In the embodiment shown, the actuation device 500 includes a neck simulator and an abdomen simulator. The neck simulator includes a plurality of electrodes at the neck. The abdomen simulator includes a plurality of electrodes at the abdomen. But in other embodiments, the electrodes can be present on only one or the other of the neck and abdomen. In some cases, one or more (or all) electrodes can be in other locations, essentially any location that contributes to causing a gag reflex and/or a Valsalva-like maneuver, or that otherwise prevents or reduces cerebral venous outflow just prior to or during an impact or a blast.

As shown in FIG. 5E, the actuation device 500 includes a turtleneck shirt 501 on which a plurality of electrodes 502 are attached. A turtleneck is illustrated in this figure, but this can be a T-shirt, a polo shirt, a button down shirt, a sweater, a sweatshirt, or any other wearable body covering (or framework/superstructure/protective gear otherwise in contact with the skin or the body). The electrodes 502 can be made of a metal or alloy, such as copper, silver, gold, etc. In some embodiments, the electrodes 502 are transcutaneous electrodes. In FIG. 5E, the electrodes 502 are visible for purpose of illustration. The electrodes 502 may be embedded in the fabric of the shirt 501 or attached to the inner side of the shirt 501 so that they are invisible. When an individual wears the shirt 501 and electrical voltage is applied to the electrodes 502, the electrodes 502 on the neck can stimulate glottis closure. And, the electrodes 502 on the abdomen stimulate the thoraco-abdominal nerves or the rectus abdominal muscles to cause abdominal muscle contraction. The electrodes 502 are distributed over an area having a size beyond a threshold (such as a threshold percentage of the individual's abdomen) so that there is enough coverage even when the shirt shifts on the body of the individual. In one embodiment, the actuation device 500 includes a sufficient number of electrodes to ensure the sufficient coverage. In another embodiment, the actuation device 500 includes one or more of electrodes that are big enough to ensure the sufficient coverage.

The electrodes 502 can be attached on the shirt 501 in different ways. In a first design 503, the electrodes 502 are attached on the inner side of the fabric 505 so that when the individual wears the shirt 501, the electrodes 502 contact with the skin of the individual. In a second way 513, the shirt includes two layers of fabric 515 and 519. There is a flex circuit 517 between the two layers of fabric. The electrodes 502 are arranged on the flex circuit 517 and embedded within the second layer of fabric 519. The flex circuit 517 can also be a flexible electrical wire. In a third design 523, the electrodes 502 are attached on the back of a layer of fabric 525. Also, the electrodes 502 are surrounded by another fabric 527. The fabric 525 and fabric 527 may be the same type of fabric.

Figure 5F:
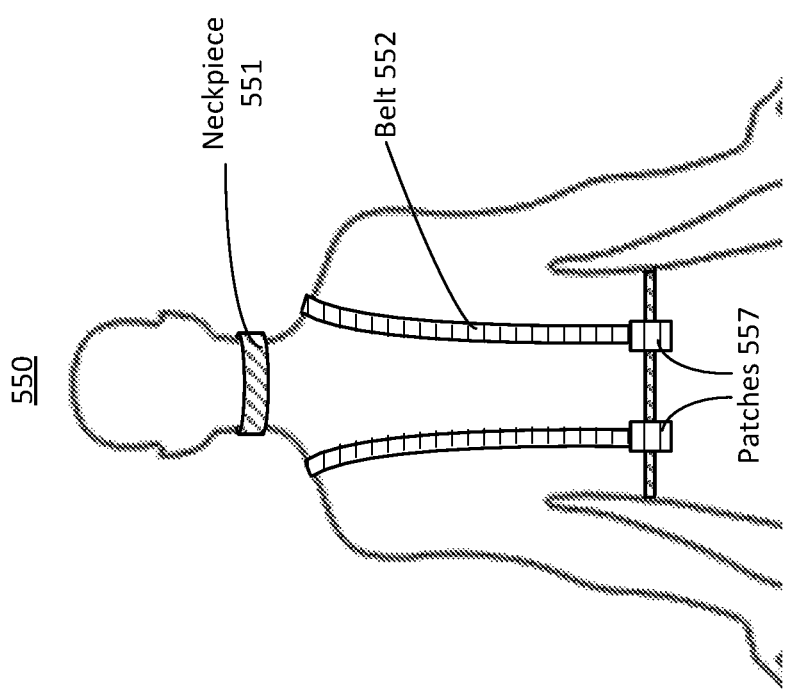

FIG. 5F shows another example actuation device 550 that is configured to cause electrical stimulation to induce a Valsalva-like maneuver, in accordance with one embodiment. In the embodiment shown, there are electrodes illustrated at both the neck and abdomen or along the torso, but design can include only one or the other of the two, as explained above for the shirt/turtleneck design (e.g., there can both a belt and neckpiece, or just one or the other). The electrodes at the neck are positioned to cause glottis closure. The electrodes at the abdomen or along the torso are positioned to cause a Valsalva-like maneuver. In some cases, one or more (or all) electrodes can be in other locations, essentially any location that contributes to causing glottis closure and/or a Valsalva-like maneuver, or that otherwise prevents or reduces cerebral venous outflow just prior to or during an impact or a blast.

Figure 5G:
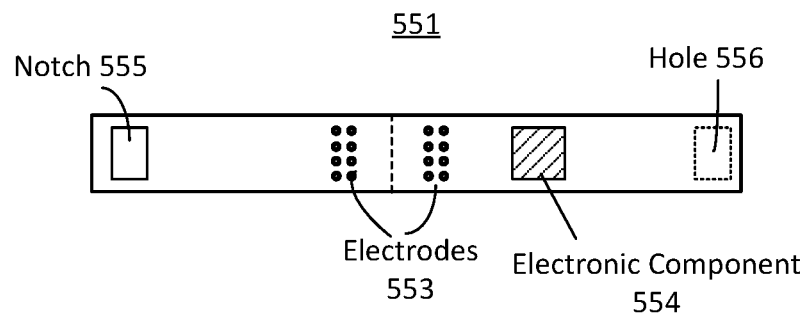

The actuation device 550 includes a neckpiece 551 and a belt 552 in this illustration. FIG. 5G shows a view of the neckpiece 551. The neckpiece 551 includes electrodes 553 that induce electrical stimulation to the neck of an individual wearing the neckpiece 553 to cause glottis closure. Additionally, the neckpiece 551 includes an electronic component 554. The electronic component 554 can be configured for communication. For example, the electronic component 554 receives signals from a controller (such as the compute ring system 120), converts the signals into electrical voltages or electrical currents for driving the electrodes 762. The electronic component 554 may also include a power source that provides power to drive the electrodes 553. In some embodiments, the electronic component 554 has computing power to determine when and how to activate the electrical stimulation. For example, the electronic component 554 receives signals indicating an event surrounding the individual from a remote sensor 125 and determines whether the event will likely cause brain injury. If so, the electronic component 554 can further determine amplitude, frequency, and duration of the electrical stimulation. The electronic component 554 and the electrodes 553 can both be attached to a flexible circuit.

The neckpiece 760 also includes a notch 555 and a hole 556 in some embodiments. The notch 555 can go through the hole 556 to close the neckpiece 551 and secure it on the individual's neck. In some embodiments, the neckpiece 760 also includes a mark (such as the dash line in FIG. 5G). The mark assists the individual to put the neckpiece in the right way so that the electrodes 553 are at the right positions of the neck to cause glottis closure.

Figure 5H:
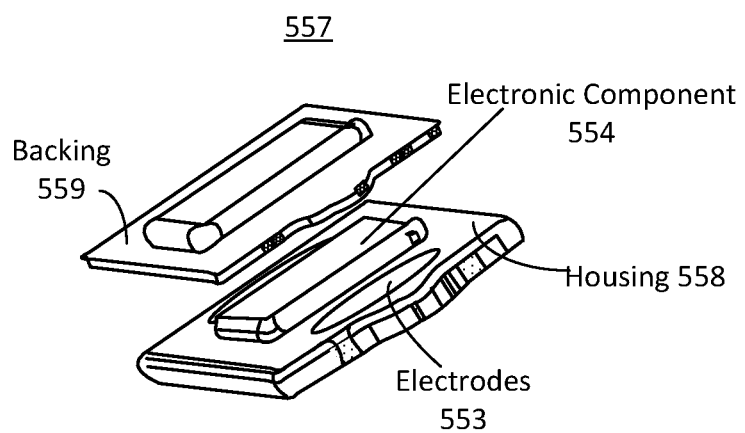
Figure 5I:
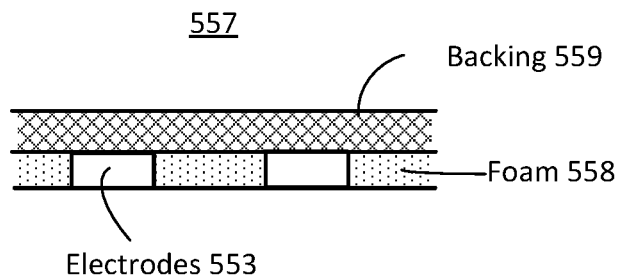

Electrodes 553 are also attached on the belt 551 so that when the individual wears the belt, the electrodes 553 can induce electrical stimulation to abdomen of the individual to induce contraction of the abdominal musculature. In one embodiment, the electrodes 553 are attached on the patches 557. FIG. 5H shows a prospective view of a patch 557. FIG. 5I shows a cross-section view of the patch 557. The patches 557 includes a housing 558, where the electrodes 553 are embedded. The housing 558 can be made of a plastic, foam, or other types of materials. In the embodiment of FIG. 5H, the electrodes 553 are round. In other embodiments, the electrodes 553 can have other shapes, such as square. In addition to the electrodes 553, an electronic component 554 is also embedded in the housing 558. The patch 557 also includes a backing 559. The backing 559 facilitates attachment of the patch 557 to the belt 552. The backing 559 can be glued onto the housing 558. In some embodiments, the patches 557 can be worn by the individual directly. Also, the patches 557 can have different shapes. For example, a patch 557 for the neck has a different shape and size from a patch 557 for the abdomen. In some embodiments, the backing 559 includes a flex circuit. The flex circuit can be made with polyimide and/or other materials.

The belt 551 can have various designs, such as a cross body design similar to a seat belt. The illustration shows two belts/straps, but there can be just one, or more than two. They can be arranged in different ways, such as going around the torso or abdomen. They can wrap entirely around the body or around just a portion of the body.

Besides the actuation devices 500 and 550 shown in FIGS. 5E and 5H, there are other designs of actuation devices for Valsalva-like maneuver. For example, an actuation device can have a neckpiece that includes electrodes to induce electrical stimulation to the neck and a shirt that includes electrodes to induce electrical stimulation to abdomen. Or an actuation device can have a turtleneck shirt that includes electrodes to induce electrical stimulation to neck and a belt that includes electrodes to induce electrical stimulation to abdomen. There can be other designs than neckpieces and belts or straps, as well. For example, any design that puts electrodes into contact with the locations of the body to simulate a gag reflex, a Valsalva-like maneuver, or any other mechanism that reduces or prevents cerebral venous outflow prior to or during an impact, blast, or other event. Also, an actuation device can be attached to an external system, such as a seat belt in a vehicle, and contacts with the body of an individual to be protected from brain injury. In various embodiments, an actuation device includes electrical, chemical, or mechanical components configured to limit danger to the individual.

Example Computing System of the System Environment

Figure 6:
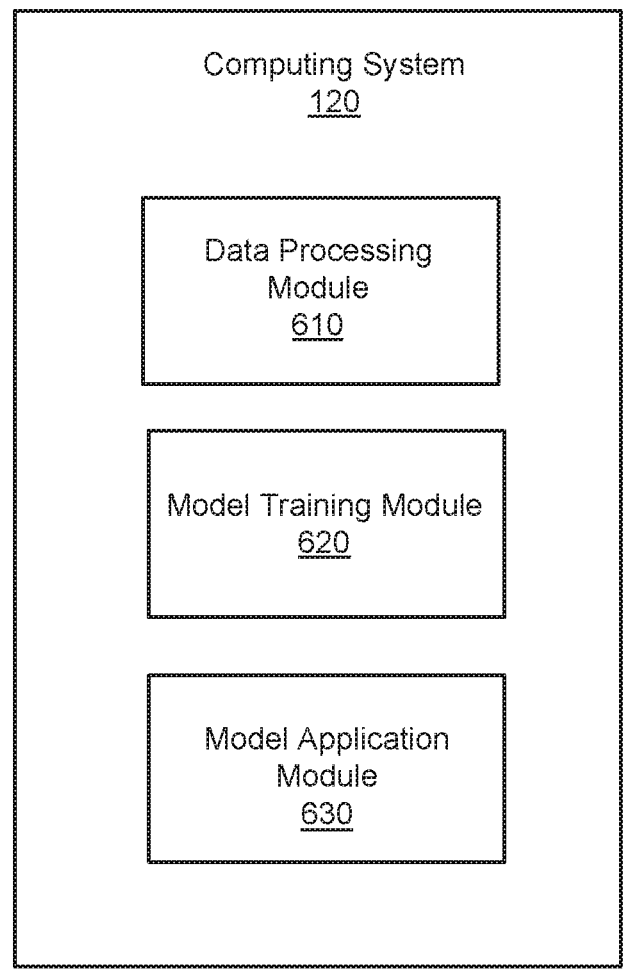
FIG. 6 illustrates an example block diagram depicting the system architecture of a computing system, in accordance with an embodiment.

FIG. 6 illustrates an example block diagram depicting the system architecture of a computing system 120, in accordance with an embodiment. The computing system 120 may include a data processing module 610, a model training module 620, and a model application module 630.

The data processing module 610 receives gathered sensor data. In one embodiment, the data processing module 610 receives gathered sensor data from the remote sensors 125 and/or from the sensors 180 of the wearable device 155. As previously described, the gathered sensor data can include orientation and/or position of the wearable device 155 as well as data corresponding to an occurring or impending collision (e.g., speed of collision). Additionally, if the system environment 100 includes multiple brain injury reduction systems 150, then the data processing module 610 can receive gathered sensor data corresponding to the relative location of a first wearable device from a first brain injury reduction system 150 to a second wearable device from a second brain injury reduction system 150. In this scenario, the computing system 120 can analyze collisions that may occur as a result of two or more wearable devices 155. This can be particularly relevant in analyzing collisions in a competitive sporting event such as a football game.

In one embodiment, the data processing module 610 may preprocess the gathered data such that the data can be subsequently analyzed. For example, the data processing module 610 can apply a filter (e.g., low pass, bandpass, or high pass) to eliminate noise in the gathered data. The processed data is then provided to either the model training module 620 for training a machine-learning model or to the model application module 630 for determination of whether a protective measure is needed.

The model training module 620 executes a machine learning algorithm using the received processed data as training data to train a machine learning model. Machine learning techniques for training the machine-learning model may be one of random forests, neural networks, naïve Bayes, support vector machines, short-term memory networks, logistic regression, bagged trees, decision trees, boosted trees and machine learning used in HIVE™ frameworks, in different embodiments.

More specifically, the computing system 120 may train a classification model such that the classification model outputs one of two possible outputs. For example, given the training data, the classification model is trained by using, as output labels, a designation of whether a protective measure is needed or not. In some embodiments, a classification model is trained specifically for an individual. In other words, a classification model can be trained to consider the personal tendencies and behavior of an individual that may change the susceptibility of the individual to brain injury. In other embodiments, the model training module 620 trains a classification model for a group of individuals that is specific for a demographic (e.g., elderly individuals) or any other characteristic (e.g., for a particular football position such as a running back, a quarterback, a linesman, and the like).

The model application module 630 applies a trained machine-learning model to newly received sensor data that corresponds to a currently occurring or impending collision. Thus, the trained machine learning model evaluates whether a protective measure needs to be performed in response to the gathered data. If a protective measure is needed, the computing system 120 provides the evaluation to the brain injury reduction system 150. Therefore, the wearable device 155 of the brain injury reduction system 150 can execute the protective measure. In some embodiments, the computing system 120 provides the trained machine learning model to the brain injury reduction system 150 such that when an occurring or impending collision is detected, the wearable device 155 can rapidly determine whether a protective measure is to be provided by applying the trained machine learning model.

Providing a Protective Measure for Reducing Brain Injury

Figure 7:
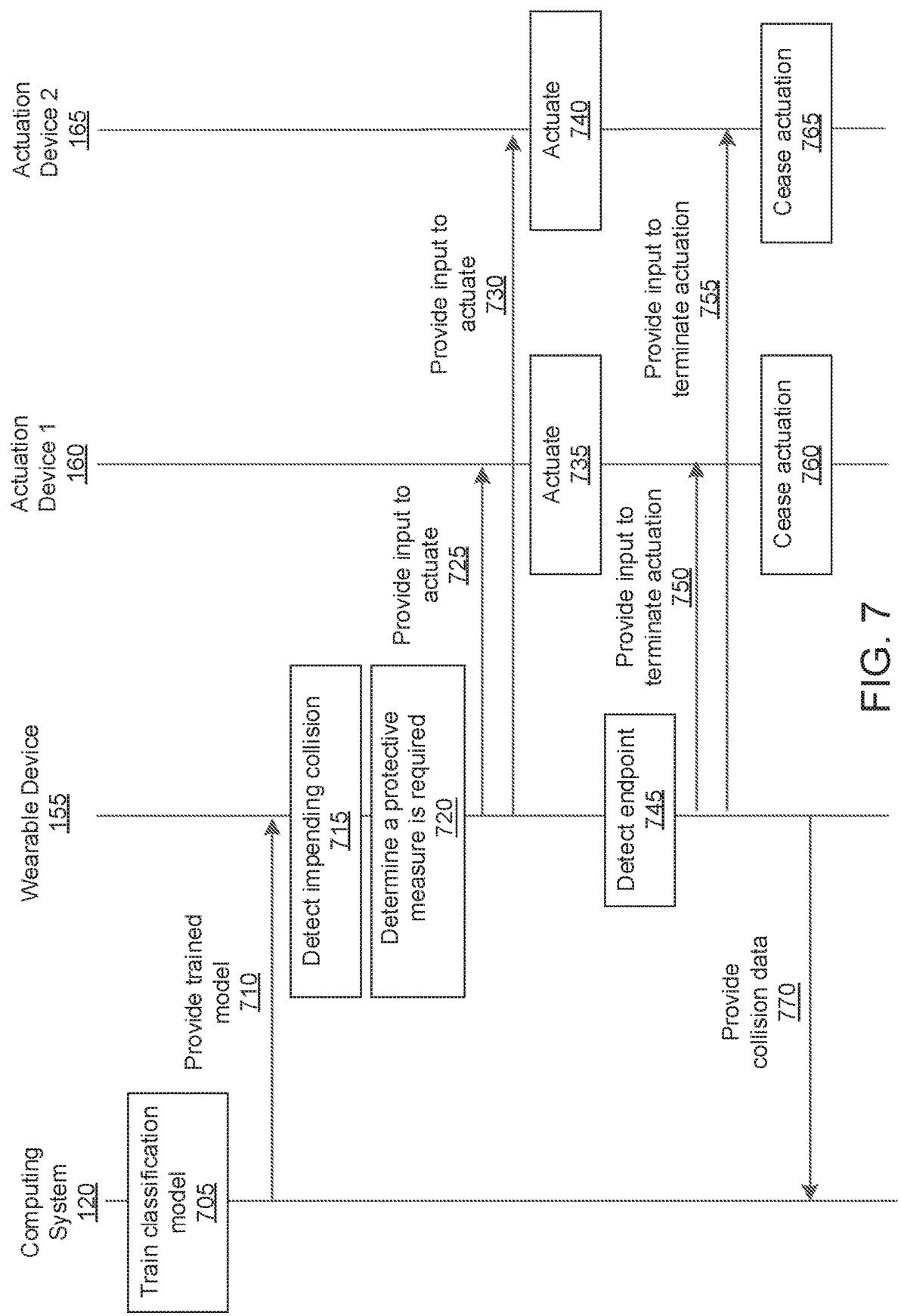
FIG. 7 illustrates an example interaction diagram for providing a protective measure for reducing brain injury in an individual, in accordance with an embodiment.

FIG. 7 illustrates an example interaction diagram for providing a protective measure for reducing brain injury in an individual, in accordance with an embodiment. In some embodiments, the process of providing a protective measure includes the wearable device 155 and one of the actuation devices 160 or 165. In various embodiments, the process need not include the computing system 120 such that detection of an impending collision by the wearable device 155 is performed autonomously.

Initially, a computing system 120 of the system environment 100 may train 705 a classification model that receives data corresponding to an occurring or impending collision as inputs, and outputs a classification as to whether a protective measure is to be provided. Generally, the classification model can be trained on training data that is derived from prior collisions. For example, training data may include data that is specific to an individual that was involved in the prior collision including, but not limited to, the orientation and/or position of the individual, the speed at which the individual was traveling, unique characteristics of the individual (e.g., reaction time), and the like. Therefore, a trained classification model may be specifically trained for a particular individual such that determination of whether a protective measure is required is specifically tailored for the individual.

As depicted in FIG. 7, the trained classification model is provided 710 to the wearable device 155 of the brain injury reduction system 150. Therefore, when the wearable device 155 detects 715 an impending collision, the wearable device 155 can rapidly determine 720 that a protective measure is required by applying the data corresponding to the impending collision to the trained classification model.

In another embodiment, the trained classification model is maintained by the computing system 120. Therefore, when the wearable device 155 detects 715 an impending collision, the data corresponding to the impending collision is transmitted to the computing system 120 to determine whether a protective measure is required. As such, the computing system 120 can provide an input to the wearable device 155 as to whether a protective measure is to be performed.

Once the wearable device 155 determines or receives instructions that a protective measure is required, the wearable device 155 provides 725 an input to an actuation device 1 (160) and provides 730 an input to an actuation device 2 (165). This input may be provided through wired or wireless communication technology (e.g., Bluetooth, NFC, WiFi, LTE, and the like). In some embodiments, the wearable device 155 only provides 730 an input to actuation device 1 (160) to maintain intracranial venous pressure by reducing venous drainage through the PVP.

Each of actuation device 1 (160) and actuation device 2 (165) actuate 735 and 740, thereby reducing venous drainage through the PVP and the IJVs, respectively. As previously described, actuation of actuation device 1 (160) may involve stimulating a gag reflex or a Valsalva-like maneuver using actuation device 1 (160). Additionally or alternatively, actuation of actuation device 2 (165) may involve external compression of the IJVs through physical structures of the actuation device 2 (165).

The wearable device 155 detects 745 an endpoint. For example, a detected endpoint may be detection of collisions. The wearable device 155 can record data corresponding to the detected collisions. As another example, a detected endpoint may be a pre-determined duration of time after the protective measure is provided. In some embodiments, the endpoint is a detected one or more collisions followed by a pre-determined duration after the detected one or more collisions. The wearable device 155 provides 750 input to the actuation device 1 (160) to terminate actuation. Alternatively or additionally, the wearable device 155 provides 755 input to the actuation device 2 (165) to terminate actuation. As such, the actuation device 1 (160) and/or the actuation device 2 (165) return to a rest state in response to the input. In some embodiments, each of the actuation device 1 (160) and actuation device 2 (165) return to an original configuration. Therefore, the individual need not endure a prolonged period of the protective measure after the collision has occurred.

In various embodiments, the wearable device 155 can provide 770 recorded collision data (e.g., orientation of the individual, imparted force, speed of collision, and the like)

to the computing system 120. As such, the computing system 120 can continue to train the classification model 705 to more accurately determine when a protective measure for the individual is required.

Figure 8:
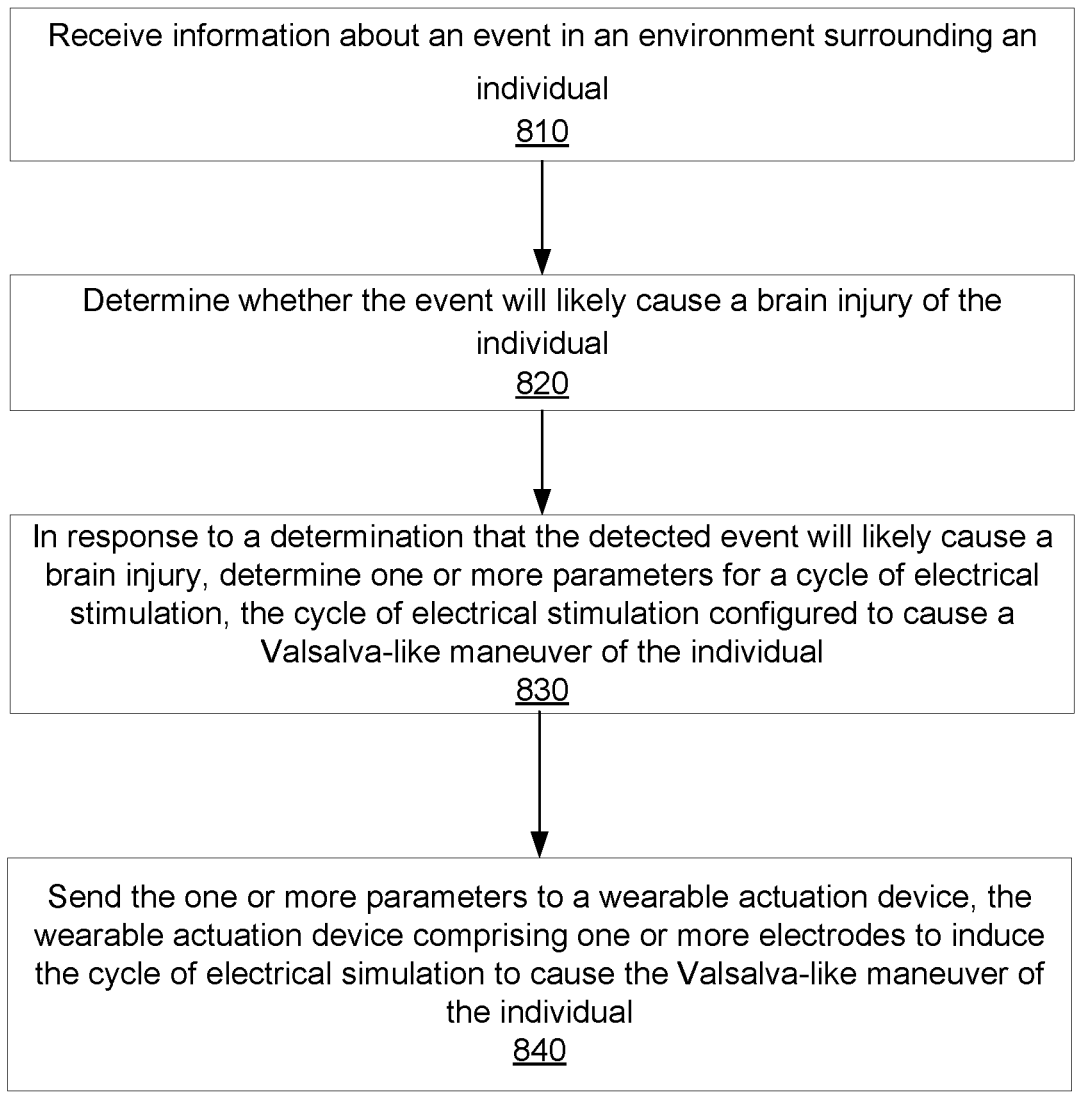
FIG. 8 is a flowchart illustrating a process inducing a Valsalva-like maneuver or a gag reflex of an individual to protect the individual from a brain injury, in accordance with an embodiment.

FIG. 8 is a flowchart illustrating a process of inducing a Valsalva-like maneuver or a gag reflex of an individual to protect the individual from a brain injury, in accordance with an embodiment. In some embodiments, the process is performed by the computing system 120, although some or all of the operations in the method may be performed by other entities in other embodiments. In some embodiments, the operations in the flow chart are performed in a different order and can include different and/or additional steps.

The computing system 120 receives 810 information about an event in an environment surrounding an individual. The information can be received from a remote sensor 125 and/or a sensor in a wearable device 155 that is configured to be worn by the individual. The information can be image data or images of the environment that show the event and the individual. The computing system 120 determines 820, based on the received information, whether the event will likely cause a brain injury of the individual. For example, the computing system 120 determines a distance between the event and the individual. The computing system 120 may also estimate severity of the event. In some embodiments, the computing system 120 inputs the information into a trained model. The trained model outputs a likelihood of a brain injury. In response to a determination that the detected event will likely cause a brain injury, the computing system 120 determines one or more parameters for a cycle of electrical stimulation. The cycle of electrical stimulation is configured to cause a Valsalva-like maneuver or gag reflex of the individual. Examples of the parameters includes an amplitude (e.g., an electrical voltage or an electrical current), a frequency of the electrical stimulation, and a duration of the electrical stimulation.

In some embodiments, the computing system 120 also receives information indicating a condition of the abdominal muscle of the individual or condition of the neck area/glottis. The computing system 120 determines a degree of muscle fatigue and determines the parameters based on the determined degree of muscle fatigue. Also, the computing system 120 may receive information indicating effectiveness of a previous Valsalva-like maneuver or gag reflex stimulation of the individual. The computing system 120 can determine the parameters based on the effectiveness of the previous Valsalva-like maneuver/gag reflex. For example, if the information indicates that the previous Valsalva-like maneuver/gag reflex was not strong enough, the computing system 120 determines that the amplitude of the cycle of electrical stimulation should be higher than the previous one, or the frequency/duration of the electrical stimulation should be higher too. As another example, if the information indicates that the previous Valsalva-like maneuver or gag reflex was too strong or stronger than needed, the computing system 120 decreases the amplitude, frequency, and/or duration of the electrical stimulation for the cycle of electrical stimulation.

The computing system 120 sends the one or more parameters to a wearable actuation device. The wearable actuation device comprises one or more electrodes to induce the cycle of electrical stimulation in accordance to the parameters to cause the Valsalva-like maneuver or gag reflex of the individual. The Valsalva-like maneuver/gag reflex increases stiffness of the brain tissues of the individual and therefore protects the individual from the brain injury that could otherwise be caused by the event.

Additional Embodiment Considerations

Throughout this specification, as used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

The term "housing" or "means for housing," as used throughout, may refer to any holder or structure that houses all or a portion of a component of the system, such as an actuation device, a sensor, or both. The term "actuation device" or "means for actuating" as used throughout, may refer to any device or entity (including mechanical, electrical, or chemical actuation devices) that interacts with the body or otherwise operates to cause a response that prevents or reduces outflow of venous drainage from the PVP, IJVs, or both (or other component via which venous drainage from the intracranial compartment occurs). The term "sensing device," "sensor," "means for detecting" or "means for sensing," as used throughout, may refer to any device capable of sensing or detecting an effect or occurrence that indicates an impending or occurring collision.

Finally, as used herein any reference to "one embodiment," "some embodiments," or "various embodiments" means that a particular element, feature, structure, or characteristic described in connection with the embodiment is included in at least one embodiment. The appearances of the phrase "in one embodiment" in various places in the specification are not necessarily all referring to the same embodiment.

Upon reading this disclosure, those of skilled in the art will appreciate still additional alternative structural and functional designs for propeller blades as disclosed from the principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement and details of the apparatus disclosed herein without departing from the spirit and scope defined in the appended claims.

What is claimed is:

1. A system for reducing a severity of a brain injury to be incurred by an individual, the system comprising:
    a wearable actuation device configured to contact the abdomen of the individual, the wearable actuation device comprising:
        one or more stimulators on or within the actuation device configured to cause an increase in intraabdominal pressure and a reduction in cerebral venous drainage;
    a sensing device in communication with the wearable actuation device configured to detect an event in an environment surrounding the individual; and
    a controller configured to:
        receive an output from the sensing device, and in response to determining, based on the output from the sensing device, that the event in the environment surrounding the individual will likely cause the brain injury:
  generate an instruction for the wearable actuation device to activate the one or more stimulators, and send the instruction to the wearable actuation device.

2. The system of claim 1, wherein the sensing device is external to the body of the individual.

3. The system of claim 2, wherein the sensing device is configured to move when the individual moves.

4. The system of claim 2, wherein the sensing device is stationary.

5. The system of claim 1, wherein the sensing device comprises one or more electromagnetic radiation sensors configured to capture data of the environment surrounding the individual.

6. The system of claim 1, wherein a stimulator comprises one or more electrodes, the electrodes distributed over an area having a size beyond a threshold.

7. The system of claim 6, wherein the electrodes include at least one of the following: one or more indwelling electrodes, one or more implanted electrode, and one or more transcutaneous electrodes.

8. The system of claim 6, wherein at least some of the electrodes are arranged in a flex circuit.

9. The system of claim 1, wherein the controller and the wearable actuation are arranged on a flexible circuit, the flexible circuit mounted to a wearable housing that is configured to be worn on the body of the individual.

10. The system of claim 1, wherein a controller is configured to determine that the event in the environment surrounding the individual will likely cause the brain injury by determining that the event will likely cause at least one of the following: a change in acceleration of the individual's head, an impact to the individual's head, or a blast to the individual's head.

11. The system of claim 1, wherein the controller is further configured to:
  receive information indicating a condition of muscle of the individual;
  determine a degree of muscle fatigue based on the received information;
  generate a second instruction based on the determined degree of muscle fatigue; and
  send the second instruction to the wearable actuation device.

12. The system of claim 11, wherein the information indicating the condition of the abdominal muscle is received from a sensor configured to detect muscle fatigue.

13. The system of claim 1, wherein executing the instruction causes the wearable actuation device to activate an electrical stimulation, the instruction comprising an amplitude, a frequency, and a duration of the electrical stimulation.

14. The system of claim 13, wherein the controller is further configured to:
  receive information indicating effectiveness of the electrical stimulation;
  generate an additional instruction to the wearable actuation device based on the received information; and
  send the additional instruction to the wearable actuation device to activate another electrical stimulation.

15. A method comprising:
  receiving information about an event in an environment surrounding an individual;
  determining, based on the received information, whether the event will likely cause brain injury of the individual;
  in response to a determination that the detected event will likely cause a brain injury, determining one or more parameters for a cycle of electrical stimulation, the cycle of electrical stimulation configured to cause a reduction in cerebral venous drainage and an increase in at least one of intraabdominal pressure or intrathoracic pressure within the individual; and
  sending the one or more parameters to a wearable actuation device configured to contact the abdomen of the individual, the wearable actuation device comprising one or more electrodes to induce the cycle of electrical stimulation to cause the increase in intraabdominal pressure within the individual.

16. The method of claim 15, wherein determining one or more parameters for a cycle of electrical stimulation comprises:
  receiving information indicating a condition of one or more muscles of the individual;
  determining a degree of muscle fatigue; and
  determining the one or more parameters based on the determined degree of muscle fatigue.

17. The method of claim 15, wherein determining one or more parameters for a cycle of electrical stimulation comprises:
  receiving feedback information associated with a previous cycle of electrical stimulation; and
  determining the one or more parameters based on the feedback information.

18. The system of claim 1, wherein the actuation device is further configured to cause an increase in intrathoracic pressure.

19. The system of claim 1, wherein the one or more stimulators include an expandable cavity and wherein executing the instruction causes the expandable cavity to expand.

20. The system of claim 19, wherein the instruction comprises one or more of a mechanical, chemical, or electrical input to cause the expandable cavity to expand.

21. The system of claim 19, wherein the wearable actuation device further comprises:
  a cartridge storing one or more of a gas, liquid, or gel; and
  one or more actuating components configured to mix the one or more of the gas, liquid, or gel stored in the cartridge, wherein mixing the one or more of the gas, liquid, or gel causes the expandable cavity to expand.

22. The system of claim 1, wherein the event includes a blast, and wherein the sensing device includes an image sensor capturing at least one or more of visible light or infrared.

23. A non-transitory computer readable storage medium comprising instructions, the instructions, when executed by one or more processors, cause the one or more processors to:
  receive information about an event in an environment surrounding an individual;
  determine, based on the received information, whether the event will likely cause brain injury of the individual;
  in response to a determination that the detected event will likely cause a brain injury, determine one or more parameters for a wearable actuation device to cause a reduction in cerebral venous drainage and an increase in at least one of intraabdominal pressure or intrathoracic pressure within the individual, the wearable actuation device configured to contact the abdomen of the individual; and send the one or more parameters to the wearable actuation device.

24. The system of claim 1, wherein the controller is further configured to:
  determine muscle contraction caused by activating the one or more stimulators; and
  in response to determining, based on a subsequent output from the sensing device, that another event in the environment will likely cause another brain injury:
    generate, based on the determined muscle contraction, another instruction for the wearable actuation device to activate the one or more stimulators.

25. The system of claim 1, wherein the controller is further configured to:
  in response to determining that two or more events that likely cause brain injuries occurred in the environment after activating the one or more stimulators:
    generate another instruction for the wearable actuation device to deactivate the one or more stimulators, wherein the one or more stimulators were held active during the one or more events.

26. The system of claim 1, wherein the wearable actuation device is configured to:
  store expandable fluids, the expandable fluids comprising one or more of a gas, liquid, or gel; and
  cause the stored expandable fluids to be mixed, wherein the mixed expandable fluids causes an extendable protrusion of the wearable actuation device to protrude from a surface of the wearable actuation device.

* * * * *